US011480641B2

(12) United States Patent
Golay et al.

(10) Patent No.: US 11,480,641 B2
(45) Date of Patent: Oct. 25, 2022

(54) PERFUSION PHANTOM FOR MRI AND AN APPARATUS, SYSTEM AND METHOD FOR VALIDATING MR IMAGES OF A PHANTOM

(71) Applicant: Gold Standard Phantoms Limited, London (GB)

(72) Inventors: Xavier Golay, London (GB); Aaron Oliver-Taylor, London (GB); Tom Hampshire, London (GB)

(73) Assignee: GOLD STANDARD PHANTOMS LIMITED

( * ) Notice: Subject to any disclaimer, the term of this patent is extended or adjusted under 35 U.S.C. 154(b) by 1093 days.

(21) Appl. No.: 16/080,895

(22) PCT Filed: Feb. 23, 2017

(86) PCT No.: PCT/EP2017/054254
§ 371 (c)(1),
(2) Date: Aug. 29, 2018

(87) PCT Pub. No.: WO2017/148805
PCT Pub. Date: Sep. 8, 2017

(65) Prior Publication Data
US 2019/0033419 A1   Jan. 31, 2019

(30) Foreign Application Priority Data

Feb. 29, 2016  (GB) ...................................... 1603511
Jan. 12, 2017  (GB) ...................................... 1700523

(51) Int. Cl.
*G01R 33/58*   (2006.01)
*C02F 1/32*    (2006.01)
(Continued)

(52) U.S. Cl.
CPC ................ *G01R 33/58* (2013.01); *A61L 2/10* (2013.01); *C02F 1/325* (2013.01); *F04B 17/03* (2013.01);
(Continued)

(58) Field of Classification Search
CPC ...... G01R 33/58; G01R 33/288; G01R 33/30; G01R 33/307; G01R 33/563;
(Continued)

(56) References Cited

U.S. PATENT DOCUMENTS 8,188,416 B2 *  5/2012  Borenstein ............. A61B 6/583
250/559.4
2009/0316972 A1  12/2009  Borenstein
(Continued)

FOREIGN PATENT DOCUMENTS

JP   2001187039 A      7/2001
JP   2009039411 A  *   2/2009 ............. A61B 6/583
JP   2015208387 A     11/2015

OTHER PUBLICATIONS

International Search Report for PCT/EP2017/054254 dated Aug. 9, 2017 (9 pages).
(Continued)

*Primary Examiner* — G. M. A Hyder
(74) *Attorney, Agent, or Firm* — Conley Rose, P.C.

(57) ABSTRACT

A perfusion chamber for use in a phantom includes a waterproof housing containing a porous material defining fluid paths between pores and tubular channels within the porous material. A reservoir for use in a phantom, a pump mechanism for use within the bore of an MRI scanner, a phantom for use in an MRI scanner, and a method for calibrating a scanning device are disclosed. Also disclosed is apparatus for validating images of a phantom that includes: one or more sensors for coupling to a phantom to be imaged;
(Continued)

a control/logging system configured to: collect sensor data during imaging of the phantom and pass this as input to a computer model; compare the image data with reference image data produced using the computer model; and return a pass score depending on the comparison. A system and method for verifying images of a phantom are also disclosed.

7 Claims, 11 Drawing Sheets

(51) Int. Cl.
    F04B 43/04      (2006.01)
    G01R 33/30      (2006.01)
    G01R 33/563     (2006.01)
    A61L 2/10       (2006.01)
    G01R 33/28      (2006.01)
    H01L 41/04      (2006.01)
    F04B 49/06      (2006.01)
    F04B 17/03      (2006.01)
    G09B 23/30      (2006.01)

(52) U.S. Cl.
    CPC ............ F04B 43/046 (2013.01); F04B 49/06 (2013.01); G01R 33/288 (2013.01); G01R 33/30 (2013.01); G01R 33/307 (2013.01); G01R 33/563 (2013.01); G01R 33/56366 (2013.01); G09B 23/303 (2013.01); H01L 41/042 (2013.01); C02F 2201/3222 (2013.01); C02F 2303/04 (2013.01); F04B 2205/09 (2013.01)

(58) Field of Classification Search
    CPC ..... G01R 33/56366; A61L 2/10; C02F 1/325; C02F 2201/3222; C02F 2303/04; F04B 17/03; F04B 43/046; F04B 49/06; F04B 2205/09; G09B 23/303; G09B 23/286; H01L 41/042; A61B 5/055; A61B 6/583
    See application file for complete search history.

(56) References Cited

U.S. PATENT DOCUMENTS

| | | |
|---|---|---|
| 2010/0331667 A1 | 12/2010 | Nelson |
| 2012/0046520 A1 | 2/2012 | Augarten |
| 2014/0133636 A1* | 5/2014 | Freeman ................ A61B 6/583 378/207 |
| 2014/0370490 A1 | 12/2014 | Iaizzo |
| 2015/0314024 A1 | 11/2015 | Khan |
| 2016/0027340 A1* | 1/2016 | Chiribiri ................ G01R 33/58 434/268 |
| 2017/0184696 A1* | 6/2017 | Zuccolotto ............. G01R 33/31 |

OTHER PUBLICATIONS

Written Opinion for PCT/EP2017/054254 dated Aug. 9, 2017 (19 pages).

Ebrahimi B. et al.: "A perfusion phantom for quantitative medical imaging", Proc. of SPIE, Medical Imaging 2008: Physics of Medical Imaging, vol. 6913, 69130W, Mar. 18, 2008 (1 page).

Oliver-Taylor, Aaron et al.: "A perfusion phantom with distinct vascular territories", Proceedings of the 2011 British Chapter of the ISMRM 17th Annual Meeting, vol. 17, Sep. 7, 2011 (1 page).

Mehrabian, Hatef et al.: "Arterial input function calculation in dynamic contrast-enhanced MRI: an in vivo validation study using co-registered contrast-enhanced ultrasound imaging", European Radiology, vol. 22, No. 8, Mar. 27, 2012, pp. 1735-1747 (13 pages).

Chiribiri, Amedeo et al.: "Perfusion phantom: An efficient and reproducible method to simulate myocardial first-pass perfusion measurements with cardiovascular magnetic resonance", Magnetic Resonance in Medicine, vol. 69, No. 3, Apr. 24, 2012, pp. 698-707 (10 pages).

Flint, Jeremy J. et al.: "A Microperfusion and In-Bore Oxygenator System Designed for Magnetic Resonance Microscopy Studies on Living Tissue Explants", Scientific Reports, vol. 5, No. 1, Dec. 15, 2015, pp. 18095-1 (11 pages).

Buskila, Yossi et al.: "Extending the viability of acute brain slices", Scientific Reports, vol. 4, No. 1, Jun. 16, 2014, pp. 5309-1 (7 pages).

Cloutier Guy et al.: "A multimodality vascular imaging phantom with fiducial markers visible in DSA, CTA, MRA, and ultrasound", Medical Physics, vol. 31, No. 6, Jun. 1, 2004, pp. 1424-1433 (10 pages).

Reischauer, Carolin: "Construction of a temperature-controlled diffusion phantom for quality control of diffusion measurements", Journal of Magnetic Resonance Imaging, vol. 29, n.3, Jan. 1, 2009, pp. 692-698 (7 pages).

Hara, Marina et al.: "A new phantom and empirical formula for apparent diffusion coefficient measurement by a 3 Tesla magnetic resonance imaging scanner", Oncology Letters, vol. 8, May 28, 2014, pp. 819-824 (5 pages).

* cited by examiner

PERFUSION PHANTOM FOR MRI AND AN APPARATUS, SYSTEM AND METHOD FOR VALIDATING MR IMAGES OF A PHANTOM

CROSS REFERENCE TO RELATED APPLICATIONS

This application is the U.S. National Stage entry under 35 U.S.C. § 371 of International Patent Application No. PCT/EP2017/054254, filed Feb. 23, 2017, and entitled "A Temperature Measuring Apparatus and a Method of Measuring Temperature," which claims priority to GB Application No. 1603511.5 on Feb. 29, 2016, entitled "A Perfusion Phantom"," and GB Application No. 1700523.2 on Jan. 12, 2017, entitled "Apparatus, System and Method for Validating Images of a Phantom" all of which are incorporated by reference herein in their entireties for all purposes.

STATEMENT REGARDING FEDERALLY SPONSORED RESEARCH OR DEVELOPMENT

Not applicable

BACKGROUND

The development of non-invasive imaging techniques is one of the most notable advances in the medical field over the past few decades. It is likely that this rate of progress will continue given the importance of achieving accurate and timely diagnoses in the safest way possible. A major step forward has been the introduction of Magnetic Resonance Imaging (MRI) in the latter part of the 20$^{th}$ century, which allowed detailed images to be taken of the inside of a patient without using invasive methods or subjecting the patient to ionising radiation. MRI utilises the spin properties of protons within the body as markers of the surrounding material. Placing the body within a strong magnetic field causes protons to align. Pulses of radio waves are then emitted which disturb the protons and force them out of alignment. Following each pulse, the protons "relax" back into their aligned state emitting radiation which can be detected by the scanner. The speed at which protons realign affects the radiation emitted as they do so and thus provides information about the surrounding material within the tissue which can be used to build up a detailed image.

Although MRI is effective at providing high resolution anatomical images, initially the method was (and for the most part still is) used only to glean information about the physical structure and material of the body rather than being usable to image organ function. For this purpose, expensive techniques such as Positron Emission Tomography (PET) are generally used. PET works by the injection of a radioactive tracer such as $^{15}$O (an isotope of oxygen) into the body. As the radioactive substance decays, positrons are emitted and can be detected. Blood diffusing into brain tissue can be imaged in this way and used to indicate regions where blood flow is greater and which are particularly metabolically active. This is an effective way of imaging brain activity (rather than just structure) but involves the introduction of a foreign substance which must be filtered by the liver and kidneys of the patient. This can present difficulties, particularly in patients with chronic kidney or liver problems.

Arterial Spin Labelling (ASL) provides a non-invasive method utilising MRI to image brain activity by allowing for the weighting of an MRI signal by perfusion, the delivery of nutritive arterial blood to an organ. ASL works similarly to PET but endogenous markers rather than radioactive tracers are used which greatly reduces risk to the patient. The method works by inverting the magnetisation of protons using a radio frequency inversion pulse within a slice just below the imaging plane. The magnetically tagged blood travels into the imaging plane and is imaged. A control image is taken in which the marker is not present. The difference between these images represents blood flow to each area within an image during a particular time period. The introduction of such methods into clinical practice would be extremely valuable in the treatment of diseases such as dementia, however at present the requisite standards are not in place.

Medical imaging has traditionally been focused on qualitative, rather than quantitative, diagnostic interpretation. This requires the presence of a trained radiologist who is able to recognise patterns in the images and link these to various physiological conditions. Quantitative medical imaging turns the imaging system into a scientific apparatus which is able to measure and quantify a particular physiological parameter. Subjectivity in the interpretation of the results is reduced; however it is vital in a medical setting that scanning devices are calibrated to international standards to ensure that measurements derived from the images provide a realistic measure of physiological properties. For this reason medical imaging is largely still based on qualitative interpretation.

In order to properly calibrate results, phantoms may be used which replicate as closely as possible the conditions within a living subject relating to properties to be imaged. Because the actual value of a measured property within the phantom is known, images taken of the phantom can be used to calibrate the scanners in order to provide an accurate measure of this property when an image of a real subject is taken. WO-A-2014/140547, for example, describes a perfusion phantom for use in contrast imaging applications. The phantom comprises four separate chambers between which perfusate flows in order to represent the ventricles and aorta of the heart.

Although such phantoms are known and have been used for research purposes to test the application of individual MRI scanners, no systems able to calibrate these scanners to a medically recognised standard have yet been designed. In particular, because ASL is a relatively new imaging technique, phantoms designed for use in MRI machines for ASL, even for research purposes, are very few and are not suitable for clinical use.

SUMMARY OF THE DISCLOSURE

This disclosure relates to a perfusion chamber for use in a phantom, a reservoir for use in a phantom, a pump mechanism for use within the bore of an MRI scanner, a phantom for use in an MRI scanner, a method for calibrating a scanning device, an apparatus for validating images of a phantom, a system for validating images of a phantom, and a method of validating images of a phantom.

According to a first aspect of the present disclosure, there is provided a perfusion chamber for use in a phantom, the perfusion chamber comprising: a waterproof housing containing a porous material, the porous material defining fluid paths between pores and tubular channels within the porous material.

A phantom is provided that is usable in calibrating MRI machines nationwide in order to be able to meet the standards applicable to medical environments. This will allow quantitative medical imaging to be widely applied in clinical environments for the first time. Due to its design and the components used in various embodiments, the present phantom is light and easy to manufacture and transport.

Such a perfusion chamber is particularly suitable for simulating the flow of blood from arteries into capillary beds, such as would occur in the brain, with the porous material itself, and pathways between the pores therein acting to simulate the capillary bed and the tubular channels the arteries.

In an embodiment, the tubular channels form a first set of tubular channels extending part way through the porous material from an inlet side towards an outlet side.

In an embodiment, the perfusion chamber comprises a second set of tubular channels extending part way through the porous material from the outlet side towards the inlet side and which are offset from the first set of tubular channels. The first set of channels extending from the inlet side represent arteries, and the second set of channels extending from the outlet side represent veins, so that the perfusate flows into the porous material through the first channels, through pathways formed by the pores and out through the second set of channels in a similar way to blood flowing into and out of a capillary bed.

In an embodiment, the housing is formed of acrylic. Acrylic is particularly suitable because it is light, easy to shape and is not affected by the strong electro-magnetic fields within the bore of a scanner (in situations where the phantom is to be used in an MRI scanner, for example).

In an embodiment, the chamber is cylindrical and arranged such that perfusate can flow from one end face towards the opposite end face through the porous material.

In an embodiment, the perfusion chamber comprises a labelling chamber through which perfusate passes before reaching the porous material. As the perfusate passes through the labelling chamber, it can be tagged for example by inverting the magnetisation of the perfusate in a slice before the perfusate reaches the porous material and so is able to replicate the flow of tagged blood or body fluid into a capillary bed during ASL.

In an embodiment, the labelling chamber is substantially filled with doped static water and comprises a tube within which perfusate can pass through the labelling chamber towards the porous material.

In an embodiment, the porous material is sintered high density polyethylene or sintered polypropylene. Sintered high density polyethylene can be easily and cheaply produced and shaped to form the block or discs or porous material for placing within the perfusion chamber. The position, size and shapes of the voids that can be produced also provide a good match to fluid flow within capillary beds when the chamber is in use and perfusate flows through it.

According to a second aspect of the present disclosure, there is provided a reservoir for use in a phantom, the reservoir comprising a waterproof housing having an inlet and an outlet between which perfusate can flow, wherein perfusate is directed to flow between the inlet and the outlet along a tortuous path that is longer than the distance between the inlet and the outlet. This configuration allows perfusate to be held within the reservoir for enough time for the longitudinal magnetisation of any tagged fluid to relax back to equilibrium before re-entering the perfusion chamber. The length of the tortuous path can be easily adapted to adjust the time spent within the reservoir (for example to suit different flow velocities or possibly different types of perfusate).

In an embodiment, the reservoir comprises a plurality of tubes fixed within the outer housing, the tubes decreasing in diameter in a direction towards the centre of the reservoir and fixed so that perfusate can flow over and under the walls of the tubes as it moves through the reservoir from the inlet to the outlet.

In an embodiment, the tubes share a longitudinal axis with the waterproof housing.

In an embodiment, the tubes also decrease in height in a direction towards the centre of the reservoir. Perfusate can thus flow over the top of one tube and downwards into the next tube providing a waterfall effect which can help the fluid move through the chamber.

According to a third aspect of the present disclosure, there is provided a germicidal device for use in a phantom, the germicidal device comprising a waterproof container that is transparent to UV light and around which perfusate within the phantom can flow, the waterproof container housing a UV lamp for irradiating the perfusate as it passes around the container. Irradiating the perfusate with UV can disrupt the DNA of micro-organisms within the fluid and help to prevent the build-up of algae and other species which will increase the longevity of the phantom.

In an embodiment, the lamp is a UVC LED lamp that emits radiation of wavelength 250-300 nm. UVC radiation is particularly effective at destroying DNA. Being solid state, a LED is ideal for use within an MRI scanner as it is minimally effected by the electromagnetic fields, has high efficiency and can be powered from a battery. In contrast filament based UVC lamps require higher voltages and use magnetic materials, making them unsuitable for use within an MRI scanner.

In an embodiment, the waterproof container is formed of quartz glass. Quartz glass is both strong and completely transparent at UVC wavelengths allowing the maximum possible dose of UV to reach the perfusate as it passes.

In an embodiment, the waterproof container is fixed within an outer container through which perfusate flows.

According to a fourth aspect of the present disclosure, there is provided a pump mechanism for use within the bore of an MRI scanner, the pump mechanism comprising a shielded enclosure housing a piezoelectric pump, pump driving circuitry, and a filter, wherein the filter is connected to the pump driving circuit and to ground via a shielded two-core cable and to the pump via an unshielded two-core cable. The operation of the filter and shielded cable blocks any radio frequency currents induced on the cable between the power amplifier and the piezoelectric pump, shunting these currents to the cable shield.

In an embodiment, the piezoelectric pump is a diaphragm pump.

In examples the pump driving circuitry comprises of a microcontroller, digital-to-analogue converter, and a power amplifier circuit that generates voltages and currents appropriate for operating the piezoelectric diaphragm pump.

According to a fifth aspect of the present disclosure, there is provided a phantom for use in an MRI scanner, the phantom comprising a closed system through which perfusate can flow comprising a pump mechanism for moving perfusate through the system, a perfusion chamber, and a reservoir.

In an embodiment, the perfusion chamber is a perfusion chamber as described above.

In an embodiment, the reservoir is a reservoir as described above.

In an embodiment, the phantom comprises a germicidal device as described above.

In an embodiment, the pump mechanism comprises a piezoelectric pump as described above.

In an embodiment, the phantom comprises the perfusate wherein the perfusate is distilled water. The NMR relaxation time of the perfusate is preferably similar to that of human blood, such as between 1600 and 1700 ms at 3.0 T. $CuSO_4$ may be added in quantities sufficient to bring the NMR T1 relaxation time of the perfusate to between 1600 and 1700 ms. This is similar to the NMR relaxation time of arterial blood in a magnetic field of 3 T and so will provide a better representation of a real subject within the scanner. The quantity of copper sulphate can be adjusted for different types of perfusate or for different strengths of scanner.

In an embodiment, the phantom comprises the perfusate wherein the perfusate is distilled water or another liquid. In embodiments, the NMR longitudinal relaxation time of said liquid, also called spin-lattice relaxation time or T1 can be adjusted through the use of additives. In embodiments, such additives can be CuSO4.

According to a sixth aspect of the present disclosure, there is provided a phantom for use in an MRI scanner, the phantom comprising a closed system through which perfusate can flow, the system comprising a pump for moving perfusate through the system, a perfusion chamber and a germicidal device, wherein the germicidal device comprises a UV lamp for irradiating the perfusate. Providing a closed system means that once the phantom has been aseptically filled, the perfusate remains within the system reducing the chances that foreign material will be introduced. In addition providing a closed system also prevents air from dissolving into the perfusate, which may cause bubbles, and therefore MR image artefacts.

In an embodiment, the germicidal device comprises a waterproof container that is transparent to UV light and around which perfusate within the phantom can flow, the waterproof container housing the UV lamp for irradiating the perfusate as it passes around the container.

In an embodiment, the perfusion chamber is a perfusion chamber as described above.

In an embodiment, the phantom comprises a reservoir as described above.

In an embodiment, the germicidal device is a germicidal device as described above.

In an embodiment, the pump mechanism is a pump mechanism as described above.

In embodiments, the phantom comprises the perfusate wherein the perfusate is distilled water. The NMR relaxation time of the perfusate is preferably between 1600 and 1700 ms. $CuSO_4$ may be added in quantities sufficient to bring the NMR relaxation time of the perfusate to between 1600 and 1700 ms.

According to a seventh aspect of the present disclosure, there is provided a method for calibrating a scanning device, the method comprising, at a central server: receiving an image of a phantom taken on the scanning device from a remote imaging centre; comparing the image to a reference image to determine a position and orientation of the phantom within the scanner; generating a simulated image of the phantom using the determined position and orientation, and comparing the simulated image to the uploaded data to generate calibration results; forwarding calibration results to the imaging centre for performing calibration of the device at the imaging centre according to the calibration results. Analysing the results centrally using tested software (and by providing phantoms which have also been standardised and tested) means that it is possible to verify that scanners undergoing the calibration process are suitable for use in a medical environment, even given the strict standards to which these machines must adhere.

In embodiments, at the central server, an image and the associated image meta-data are received. The image may in any appropriate or convenient format, such as the original DICOM image format, although the meta-data would preferably be similar to the DICOM header data. There may be some additional information reported from the phantom e.g. perfusate temperature.

In an embodiment, the method comprises repeating the method until the calibration results indicate that the medical device is calibrated.

In an embodiment, when the device is determined to be calibrated, the method comprises forwarding a certificate to the imaging centre.

According to an eighth aspect of the present disclosure, there is provided a perfusion chamber for use in a phantom, the chamber comprising a waterproof housing containing a permeable material with tubular channels therein.

In an embodiment the perfusion chamber contains a generally solid body of permeable material with one or more tubular channels formed herein. When liquid is introduced to the housing it will preferentially first flow into and along the channels but will perfuse through the generally solid but permeable material as well. In a number of the aspects of the invention described herein the permeable material is porous. Porosity represents one way by which the permeability may be achieved, but not the only way. Other forms for the material which would provide permeability but not be porous include dialysis tubing, fibrous materials or membranes. Where appropriate, any of the embodiments described above could also be provided with this eighth aspect of the disclosure.

According to a ninth aspect of the present disclosure, there is provided a perfusion chamber for use in a phantom, the perfusion chamber comprising a porous material defining fluid paths between pores and tubular channels within the porous material.

According to a tenth aspect of the present disclosure, there is provided an apparatus for validating images of a phantom, the apparatus comprising: one or more sensors for coupling to a phantom to be imaged, the sensors being configured to measure parameters associated with the operating state of the phantom; a control/logging system configured to: collect sensor data during imaging of the phantom by an imaging system and pass this as input to a computer model; compare the image data with reference image data produced using the computer model; return a pass score or a fail score in dependence on the comparison.

In embodiments, the sensors are configured to detect and measure one or more of the temperature of fluid within the phantom, the pressure of fluid within the phantom, and the flow rate of fluid within the phantom.

In embodiments, the apparatus comprises a transceiver box located in the vicinity of the imaging system, wherein sensor data is transferred to the transceiver box via a wireless connection and passed from the transceiver box to the control/logging system using a wired connection.

In embodiments, the wireless connection is a Bluetooth connection and the wired connection comprises one or more optical fibers.

In embodiments, the control/logging system is configured to synchronise its time clock with that of the imaging system.

In embodiments, the synchronisation comprises receiving a synchronisation signal from the imaging system.

In embodiments, the synchronisation comprises using an internet based time server to provide a reference time source.

In embodiments, the predetermined threshold level is based on ISO standards.

According to an eleventh aspect of the present disclosure, there is provided a system for validating images of a phantom, the system comprising: an imaging system; a phantom to be imaged; one or more sensors coupled to the phantom to be imaged, the sensors being configured to measure parameters associated with the operating state of the phantom; a control/logging system configured to: collect sensor data during imaging of the phantom by the imaging system and pass this as input to a computer model; compare the image data with reference image data produced using the computer model; return a pass score or a fail score in dependence on the comparison.

According to a twelfth aspect of the present disclosure, there is provided a method for validating images of a phantom, the method comprising: (i) coupling sensors to the phantom for measuring parameters associated with the operating state of the phantom; (ii) placing the phantom and sensors within the imaging volume of an imaging system; (iii) simultaneously collecting sensor data and imaging the phantom using the imaging system; (iv) producing reference image data using the sensor data as input to a computer model; (v) comparing the image data with the reference image data; (vi) returning a pass score or a fail score in dependence on the comparison.

In embodiments, the method comprises making adjustments to the imaging system and repeating steps (ii) to (vi) if a fail score is returned in step (vi).

In embodiments, the method comprises making adjustments to the phantom and repeating steps (ii) to (vi) each time a fail score is returned until a pass score is returned.

In embodiments, the method comprises checking, using the sensor data, that the phantom was operating within a specified range of states for at least a specified proportion of the imaging time and returning a fail score if the phantom was not operating within the specified range of states.

In embodiments, the proportion of the imaging time is the entire imaging period.

In embodiments, the method comprises matching the orientation of the image data and reference image data prior to the comparison stage.

In embodiments, markers on the phantom are used to match the orientation.

According to a thirteenth aspect of the present disclosure, there is provided a computer programme configured to perform the method described above.

BRIEF DESCRIPTION OF THE DRAWINGS

Exemplary embodiments will now be described in detail with reference to the accompanying drawings, in which.

DETAILED DESCRIPTION OF THE DISCLOSED EXEMPLARY EMBODIMENTS

Figure 1:
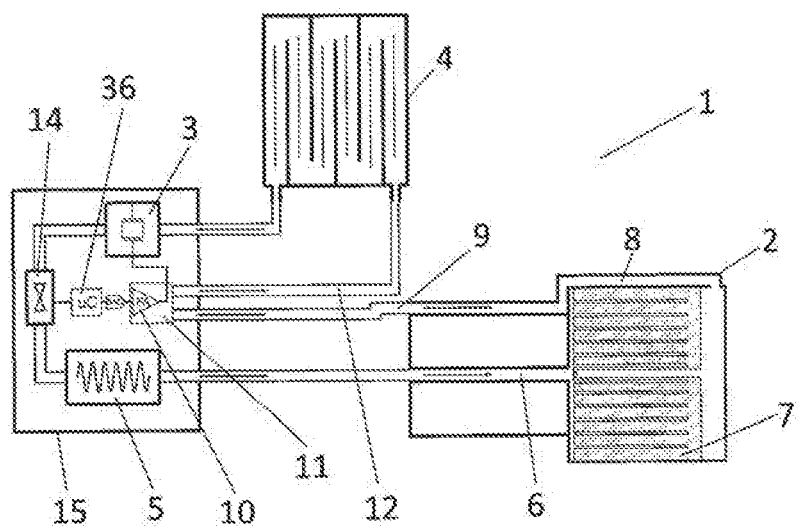
FIG. 1 shows a phantom including a perfusion chamber, reservoir and pump.

FIG. 1 shows an example of a phantom 1 for use in an MRI scanner. The phantom includes a perfusion chamber 2, through which perfusate flows in use, and a pump 3. The phantom may also include a reservoir 4, a UV-C irradiating chamber 5, and bubble traps and/or other ancillary components. The perfusion chamber 2 is designed to replicate perfusion within the body, such as within capillary beds and is particularly suitable for testing MRI scanners for use in brain imaging with ASL. The system functions as a closed system so that perfusate flows out of the pump and through all of the components of the system via a series of tubes. Once the perfusate has passed through all components it returns to the pump and is again directed through the system. FIG. 1 shows the perfusion chamber 2 into which perfusate flows via inlet 6 through a permeable medium 7 forming a portion of the chamber and out again through outlet 8. In this example the permeability of the material is achieved through the use of a porous material although other forms or structures for the material 7 could be used that also provide the requisite permeability. For example instead of a porous material, a filamentary material could be used in which a semi-compacted structure of filamentary elements is provided with spaces in between individual elements so as to achieve a degree of permeability to a liquid when forced through the medium 7 at some pressure.

In the following description reference will be made to examples in which the medium 7 is provided by a porous material. However, in view of the indication above this is not to be construed as the exclusive means of achieving permeability.

The perfusion chamber itself and possible modifications thereto is described in greater detail below. Once fluid has exited the chamber it flows through tube 9 to return to the pump where it passes through a heat exchanger 11 that actively cools the high voltage amplifier 10 that drives the piezoelectric pump, and is directed towards reservoir 4 through tube 12.

After moving through the reservoir and out of outlet tube 13, the perfusate reaches the pump 3. Before returning to the perfusion chamber, the perfusate passes through a flow meter 14 (optionally an optical flow meter) which provides constant feedback to a microcontroller 36 connected to the pump via a digital analogue converter and the high voltage amplifier. The microcontroller 36 runs a proportional-integral-derivative (PID) algorithm to provide closed-loop control of flow through the system. If the flow rate within the phantom is lower or greater than is desired then the amplitude of the driving waveform to the pump can be adjusted to bring the flow rate to its optimum value. After the flow meter, the perfusate passed through a UV treatment chamber 5 which treats perfusate passing through in order to prevent the build-up of living organisms within the system. One or more of the piezoelectric pump (or pumps), associated electronics, germicidal UV LED, and flow meter can be housed within an enclosure 16 which provides effective shielding against the intense electro-magnetic fields within the bore of the scanner. The enclosure may be formed of aluminium.

The perfusion chamber 2 and pump 3 can be fixed to a sheet of material, such as PVC, to allow it to be transported within a protective case. The particular order of the elements 2-14 shown in the figure can be changed. FIG. 1, for example, shows the perfusate flowing from the perfusion chamber through a cooling block to the reservoir before flowing through the pump (which in this example also contains a flow-meter for controlling the flow rate and a UV chamber to treat the perfusate). In an alternative embodiment, the perfusate could flow from the pump to the reservoir directly and then to the perfusion chamber. The embodiment shown, however, is more effective perfusion chamber because when fluid passes through the reservoir just prior to passing through the pump bubbles are prevented from building up in the pump, which can be problematic. Parts of the system may be detachable and re-attachable to each other to facilitate transport and/or separate replacement in the event of fault or malfunction.

In use, the phantom is substantially filled with perfusate (and may be entirely filled so that no air is present within the system). A good choice of fluid for this purpose is distilled water with a copper sulphate ($CuSO_4$) additive. Ideally enough copper sulphate should be added to bring the NMR relaxation time of the fluid to the same as or similar to the NMR relaxation time of arterial blood in a magnetic field of 3 T (around 1664 ms). The amount of copper sulphate can be adjusted depending on the particular scanner used, although for the purposes of manufacture it may be advantageous to use the same composition for the perfusion fluid in all phantoms. Ideally, the filling process should be aseptic to avoid the introduction of bacteria and other microorganisms.

The length, size and orientation of the tubing or flow pathways between components of the system can be varied although it is preferable that the overall structure is fairly compact in order to facilitate transport and use within the MRI scanners. In the absence of a reservoir in the form of a housing similar to that shown in FIG. 1, the length of the tubing can be adjusted to regulate the flow time between passes of the perfusion chamber. In other words, an extended length of tubing can function as the reservoir itself.

Figure 2A:
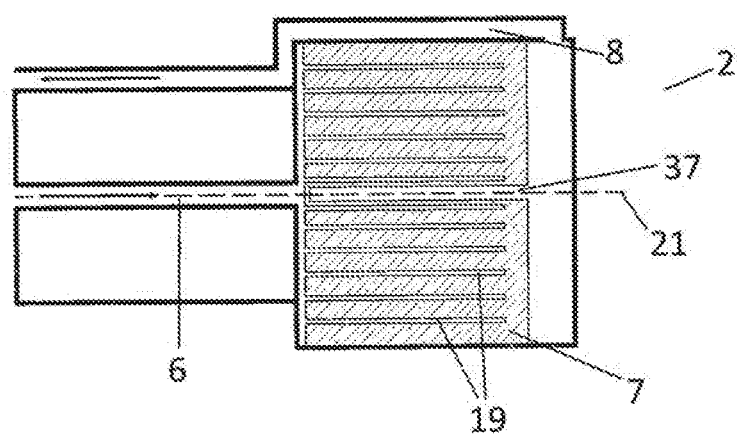
FIG. 2A shows a perfusion chamber.
Figure 2B:
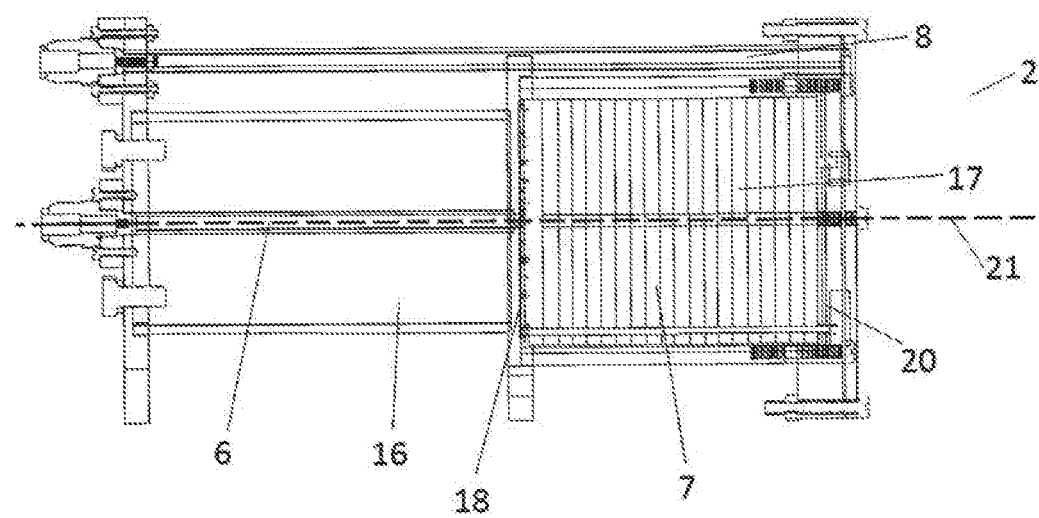
FIG. 2B is a more detailed view of a perfusion chamber.

The perfusion chamber is shown in detail in FIGS. 2A and 2B. The chamber 2 is comprised of two distinct sections which are not in fluid contact. Preferably, the chamber 2 as a whole defines a waterproof housing in which the two distinct sections are formed. The chamber 2 includes the inlet 6 and outlet 8, and the wall (typically cylindrical) surrounding the porous material, which all serve to confine, or define direction for liquid flow.

The first of the two sections is the labelling chamber 16 which can be filled with doped water that is substantially static. This water is required to ensure that the magnetic environment surrounding the inflow tube is homogeneous. The water is doped in order to control the T1 and T2 relaxation times for an optimal signal and static so that it will not be tagged along with the perfusate. The labelling portion need not necessarily be filled with doped water. It could, for example, also be filled with a gel such as agarose.

The second chamber or section 17 contains a porous material 7 and in use has perfusate flowing (pumped) through it. It is the second chamber which will be imaged when inside the MRI scanner and it is this portion which is intended to replicate as closely as possible the flow of fluid through tissue within the body (and particularly within the brain). In order to do so the particular material used and the flow channels provided within the material must be carefully chosen.

The porous material 7 may be sintered high density polyethylene (HDPE) and preferably has a high void volume (between 20% and 90% void, more preferably between 40% and 80% and most preferably about 60%) with a mean void diameter of between 10 and 50 microns. Of course, the shape of the voids may not be spherical in which case the diameter mentioned may correspond to the largest distance across the void. Inflowing perfusate enters the second chamber via the inflow tube and an inflow plate 18 which restricts the flow of fluid into the porous material to specific, distinct locations which form the ends of tubular pathways provided through the porous block. These are in addition to flow paths provided by connecting voids. Inlet and outlet plates may be formed of a non-porous material with holes that allow flow through in precise locations. In an embodiment these can be formed of acrylic with holes drilled to match the channels. It is also possible for either the inlet or outlet plate and corresponding channels to be dispensed with. The inlet or outlet side will then comprise only an end of the porous block through which fluid can enter or exit the material.

The channels are provided within the porous material to replicate flow through arteries, or the arteries and veins. Preferably, a number of narrow channels 19 are provided through the material extending from the inlet plate of the second chamber towards the outlet plate 20 in a direction that is substantially parallel to the central axis 21 of the perfusion chamber. The channels 19 may not extend all the way through the block of porous material but will generally extend to over halfway through the chamber. Perfusate enters the chamber through these channels and diffuses outwards into the porous material through the voids. The channels can be provided by drilling through the porous material and may have a diameter in the range from 0.5-2 mm (and preferably will have a diameter of around 1 mm). Alternatives to narrow channels (19) in a direction substantially parallel to the central axis may be used. For example, bifurcating channels could be used.

These channels (as well as the additional channels extending from the outlet plate described below) may be tubular in that they are elongated and formed of a continuous surface (aside from the effects of voids adjacent to the channel edge). In embodiments, the cross section taken in a direction perpendicular to the longitudinal axis of the channel may not vary substantially along the length of the channel (although in others the tubular channel may change in width along its length). The channels may be substantially straight and may also be arranged such that they extend in a direction generally parallel to the central longitudinal axis of the perfusion chamber (the central axis referred to is shown in FIG. 2A as line 21). In embodiments, the channels have a circular cross section. The channels may have a cross sectional diameter that is larger than the mean diameter of the pathways provided between voids in the porous material itself. The diameter of the pathways may refer to the largest measurement taken from one side to another of the pathways in a direction perpendicular to the flow through the pathway at any point. This will not be much larger than the average size of one void or pore.

Additional, similar channels may extend from the outlet plate 20 towards the inlet plate 18 in a direction that is substantially parallel to the central axis 21 of the chamber (although this is not essential). This second set of channels may be offset from the first and again may not extend the full way through to the inlet plate surface, but generally will extend to over halfway. Perfusate that has seeped into the porous material through voids may make its way into the second set of channels and move towards the outlet plate via this route. The first set of channels are intended to replicate arterial flow into a part of the body (i.e. the brain) and the second set to represent venous flow out of the same region. Because neither set of channels extends the whole way through the porous block, perfusate must seep through voids in a similar manner to blood passing through a capillary bed. The second set (and indeed the first set) of channels may simply be a single channel, for example a single channel running along the longitudinal axis of the porous block where the porous block is formed as a cylinder. Where a single channel is used, this may generally be wider and may have a diameter of between 1 and 4 mm. FIG. 2A shows an embodiment with a single return channel (indicated by numeral 37 in the figure).

In an embodiment, the porous block is made up of several disks or plates of sintered HDPE (or other porous material) placed close together (as shown in FIG. 2B). These may be cylindrical which helps to ensure that the conditions of flow within the perfusion chamber are uniform. The cylindrical shape of the chamber is also advantageous because of the cylindrical shaped bore of the scanner into which it must fit and because it provides a better approximation to the human head. The discs should be firmly pressed together in order to avoid any leakage therebetween and for similar reasons should fit snugly within the outer housing of the chamber. Rods can help with this, and can be placed through the set of disks to hold them in place. It is important that the channels extending through adjacent plates are aligned and including one or more rods (and preferably several spaced throughout the structure) can also ensure alignment of the channels. Producing the porous block using stacked discs in this way provides a design that is adaptable and easy to assemble. The porous block can also be formed as a whole using a method such as 3D printing or by cutting from a larger block or forming as a larger block. Using a block rather than a number of stacked plates has the advantage that unwanted leakage cannot occur between the plates; however producing or cutting a larger block can be more difficult manufacturing-wise and the use of 3D printing may lead to powder being trapped within the voids or pores after manufacture which is not ideal. Each disk in a stack may be approximately 4-30 mm thick and a CNC router may be used to drill the channels through the discs after they have been formed into the desired shape. The porous HDPE can be accurately machined using a high speed spindle with sharp, single fluted carbine tooling. Feeds and speeds are similar to those used for other foam materials. Due to the fragility of the material, a distributed fixturing technique such as vacuum hold down is recommended. Alternatively, each disc could be directly sintered in a mould, avoiding the need for any machining/further processing.

In order to test the permeability of the sintered material to determine whether the correct characteristics for use in the perfusion chamber are present, it is possible to use a small chamber comprising an acrylic tube, a calibrated flow meter, a small pump, and a differential pressure manometer. By passing fluid through the chamber with a sample of the porous material within, the pressure difference across the sample can be measured for different flow rates. A microcontroller similar to that used in the phantom itself uses the flow rate measured by the flow meter as input to a PID controller in order to maintain a stable flow rate. The measured pressure difference is indicative of the permeability of the material under test.

Any air bubbles within the perfusion chamber can affect an acquired image because the different magnetic susceptibility of air and water will have a severe impact on the magnetic field homogeneity and the signal within the porous medium. In addition, air within the porous medium may displace the perfusate so that the volume of perfusate within the porous structure is altered. This is important when using the phantom to calibrate a scanner in a clinical environment because the spatial distribution of the perfusion will not match that predicted by simulations. In order to ensure that the porous material is wet fully (no air bubbles) during use, it is possible to submerge the porous block or discs prior to use while subjecting the same to a vacuum (by submerging the discs within a container placed in a vacuum chamber, for example). Preferably, the vacuum will be as close to a perfect vacuum as possible. A −0.9 bar vacuum provides good results. A stepping motor and timing pulley system can be used to agitate the material during this process to more effectively expel air. The porous material may be both agitated and rotated about a central axis (whilst orientated horizontally or vertically) and rotation can be in more than one direction, for example the porous block or the porous discs may be rotated first clockwise, and then anti-clockwise in order to achieve the maximum air removal from the material. Rotation can be beneficial because larger bubbles will form on the surface of the porous material during the process and rotation particularly can help to coax these into detaching.

The technique described above has been found to be effective in minimising air bubbles within the material. The treated discs or block should then be loaded into the chamber body while both are submerged to avoid the trapping of any further air bubbles. Alternatively, the process can be carried out with the porous discs or block in-situ within the perfusion chamber and/or the phantom. In addition, the sintered plastic can be treated so that it is substantially hydrophilic which will aid the expellation of air bubbles.

Both chambers may be formed of acrylic which is waterproof, light and suitable for subjecting to the strong electromagnetic fields within the MRI scanner. Any suitable polymer may be used to form the chambers and in an embodiment the chambers may be formed of a mixture of different materials. The housing may be in the form of tubes closed at the ends by circular sheets. This type of acrylic casing is easy to shape (for example using a CNC router) which results in a final product that can be manufactured cheaply in high volume. Injection moulding or resin casting can be used to produce the chambers in a manufacturing setting if a suitable polymer is used.

In this example, the inflow tube extends through the centre of the labelling chamber to the chamber containing the porous block and the outflow tube runs from the upper side of the housing and along the top portion. During a scan, the perfusate can be subjected to a radio wave pulse in the labelling chamber which inverts the magnetisation of the perfusate (as would occur in the tagging plane of a subject during an ASL scan). This can be done continuously (similar to a CASL procedure) or in individual bursts to produce slices of fluid having inverted magnetisation. As the magnetised fluid passes through the second chamber and through the porous material an image is taken. A control image is also taken with perfusate for which the magnetisation is not inverted and the difference between the two provides a final image.

Figure 3:
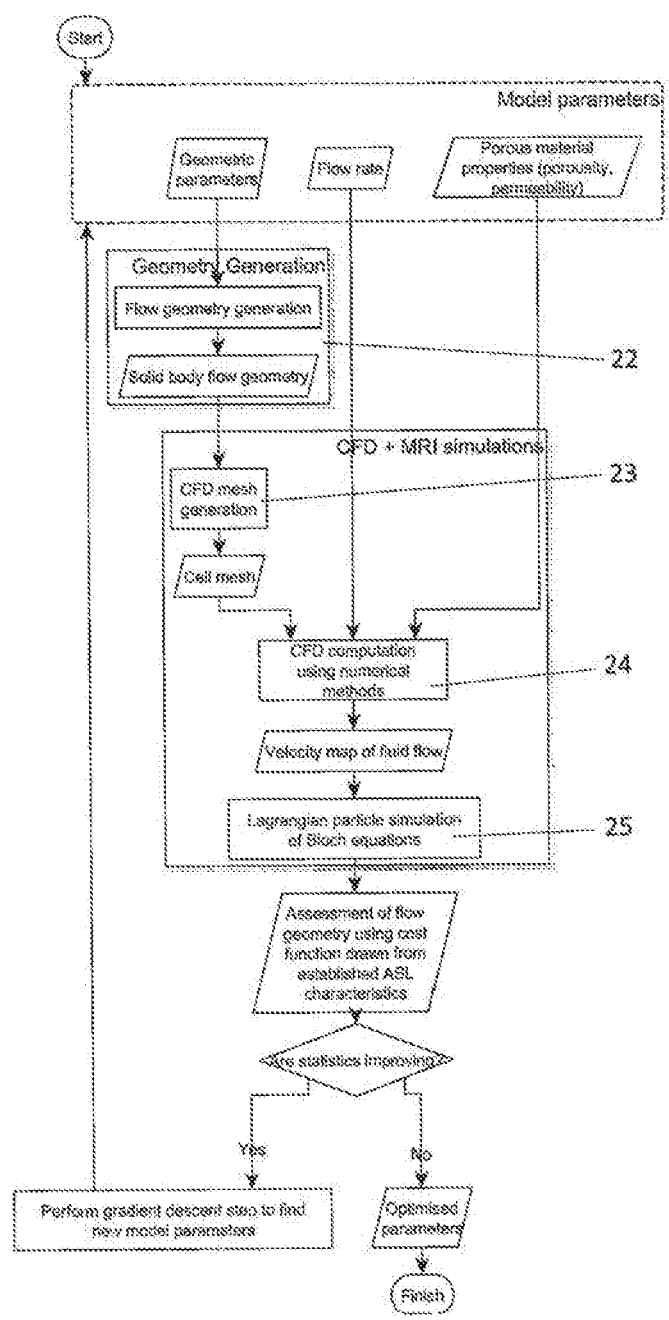
FIG. 3 is a flowchart showing a procedure for optimising flow geometry.

Generation of an optimal geometry for the perfusion chamber is achieved by way of a computerised optimisation procedure. FIG. 3 shows a flow chart of this process. In brief, initial values for input parameters representing the geometry of the perfusion chamber, permeability of the porous material, and the input flow rate are chosen and an initial flow geometry is set up at block 22. This geometry is processed to create a mesh suitable for a computational flow dynamics (CFD) simulation at 23, which uses as inputs the various initial values of the parameters provided. The fluid flow is computed using the flow geometry as input at 24 after which a particle simulation of Bloch equations is solved for the transient fluid magnetisation information (25). The output is quantified and used to optimise the perfusion chamber geometry by an iterative procedure in which input parameters are adapted.

Figure 4A:
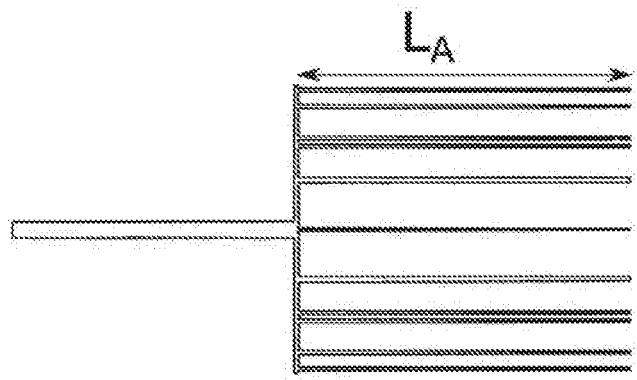
FIG. 4A illustrates how the channel length is measured.
Figure 4B:
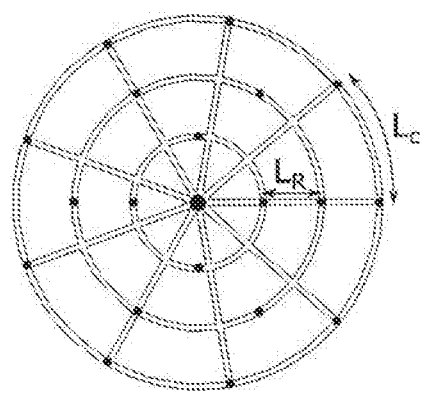
FIG. 4B illustrates how the radial and circumferential channel spacings are measured.

In more detail, an initial geometric design for the chamber is chosen using sensible values for a set of parameters to be optimised. These parameters may include the artery or channel length as a function of porous material length (the length of the inlet channels divided by the length of the porous block as shown in FIG. 4A by distance $L_A$), channel radii, the length of output channels or "veins" as compared to the length of the porous block, the inflow rate of the perfusate, the radial spacing of the channels and the circumferential spacing of the channels as shown in FIG. 4B ($L_R$ and $L_C$ respectively). The radial and circumferential spacing of the channels are relevant for a cylindrical or tubular perfusion chamber; however the distances between channels can also be parameterised as horizontal and vertical distances for a differently shaped chamber, such as a rectangular chamber.

The radius of each channel may vary with the distance of the channel from the centre of the chamber. In embodiments where a cylindrical chamber is used, a polynomial parametrisation is used to determine the radius for each channel: $R=R_0+R_1\times i$, where i is equal to the ring number (the central channel being numbered 0 and the number increasing for rings outward of the central channel as shown in FIG. 4B), $R_0$ is the zero order channel radius (fixed at between 0.5 and 2 mm) and $R_1$ is the first order channel radius (also fixed at between 0.5 and 2 mm). The radius of the central channel will thus be between 0.5 and 2 mm and the ring outward of this between 1 and 4 mm.

This polynomial parametrisation is merely an example of a possible way to parameterise a varying vessel radius. In fact, in one exemplary embodiment, the optimal radius for all arterial vessels was determined to be 0.5 mm. Due to manufacturing constraints, in any event this is a typical minimal allowed value. In one example it could be that the vessels or channels are allowed to get thicker, as they get further from the centre. In general, the parameterisation allows the optimisation to explore a greater variety of geometric configurations.

The geometry is optimised such that the resulting perfusion is analogous to key parameters defined in the ASL perfusion model literature, for example the recent ASL "White Paper": http://www.nbci.nlm.gov/pubmed/26510993, the entire contents of which are hereby incorporated by reference. These are:

Perfusion rate (CBF) within the imaging volume
  Arterial transit time (time perfusate takes to travel from the labelling region to a voxel within the imaging volume)
Velocity of the perfusate within the labelling region
FOV coverage
Pulsed ASL bolus length
Labelling region magnetic homogeneity The model may also put the following restrictions on the flow geometry: the distribution of fluid is homogeneous throughout the porous material; transit time to the porous material from the inlet is minimal. It is also preferable that manufacture of the design be as simple as possible in order to reduce the likelihood of error introduced during manufacture effecting the configuration of the perfusion chamber. The table below shows example ranges for a selection of input parameters. These ranges correspond to the range of values which can be used as input in respect of each parameter during the optimisation procedure. In general, these correspond to the maximum and minimum expected values for these parameters within the body of a subject (such as in the brain or another organ comprising arteries, veins and a capillary bed or tissue through which blood or other fluid may flow). The first set of channels extending from the input plate will thus be sized to correspond to produce flow that replicates flow through arteries and the second set through veins. The pore sizes or at least the permeability of the porous material should preferably correspond to values within capillary beds or tissues for blood or fluid flowing through these. The porous material may be treated macroscopically in the simulations. In particular, various parameters of the material (such as the permeability) can be measured and used as input for the CFD modelling.

| Model Parameter | Range |
| --- | --- |
| Channel length/length of porous material | 0-1 |
| Inflow rate | 100-700 ml/min |
| Zero-order channel radius | 0.5-2 mm |
| First-order channel radius | 0.5-2 mm |
| Radial channel spacing | 4-60 mm |
| Circumferential channel spacing | 4-60 mm |

By creating the geometry various boundary conditions are defined (such as the requirement of a zero velocity for the fluid at the edge of the chamber), which are used as input to the CFD simulation along with the inlet flow rate. The CFD simulation involves solving the Navier-Stokes equations for laminar flow using the defined boundary conditions. The result of the simulation is a velocity field for a single-phase flow with constant density and viscosity. It is conceivable that more complex modelling could be undertaken, however a simple model such as that described provides good results and is more easily updated and maintained. Different densities in any one or more of the fluid, fluid temperatures and viscosities or a consideration of possible turbulence within the fluid could, however, be introduced.

Figure 5:
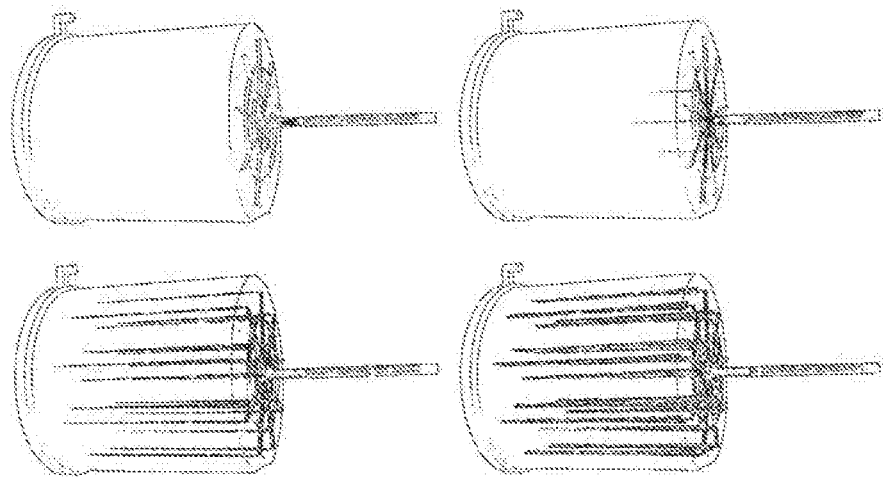
FIG. 5 shows a particle simulation of flow within an perfusion chamber during tagging.

In order to accurately simulate the properties of the fluid flow, the fluid is modelled as a set of particles, each of which represents a unit volume of fluid. By using a lagrangian representation of the water volume, the effects of the magnetic field and the velocity field (rate of flow at different points) on the positions and magnetisation of the particles of fluid over time can be tracked. The particles are subjected to a magnetic field having field strength and direction represented by a vector quantity $B_0$ which represents the main, constant magnetic field within an MRI scanner. During tagging, the particles are further subjected to a magnetic field $B_1$ which represents the radio frequency field applied to invert the magnetisation. The positions of the particles are updated at each time step using the input velocity field. As the simulation runs the component of the magnetisation vector of the particles along the $B_0$ direction recovers with respect to $T_1$ relaxation (longitudinal relaxation time) according to the equation $M_{t+\Delta t}=M_t+((1-M_t)\times\Delta t)/T_0$ where $M_{t+\Delta t}$ is the component of the magnetisation vector of the particle at time $t+\Delta t$, $M_t$ is the same at time t, and $\Delta t$ is the time step size. In order to simulate the effects of tagging the fluid, the longitudinal magnetisation is inverted (a full or partial inversion dependant on tagging efficiency) by approximating a full inversion in a given plane or slice (of all fluid within that slice) during a short period in the simulation equivalent to the labelling period during an ASL procedure. The labelled fluid then relaxes as it moves through the simulated perfusion chamber. FIG. 5 illustrates the effect of tagging the fluid particles in the simulation. The fluid is initially completely relaxed at A as it enters the porous material through the inlet tube. The magnetisation is inverted at the inlet (colour change in image B) and the colour of the fluid changes slowly back to its initial colour (indicating relaxation of the fluid) as it moves through the perfusion chamber.

Figure 6A:
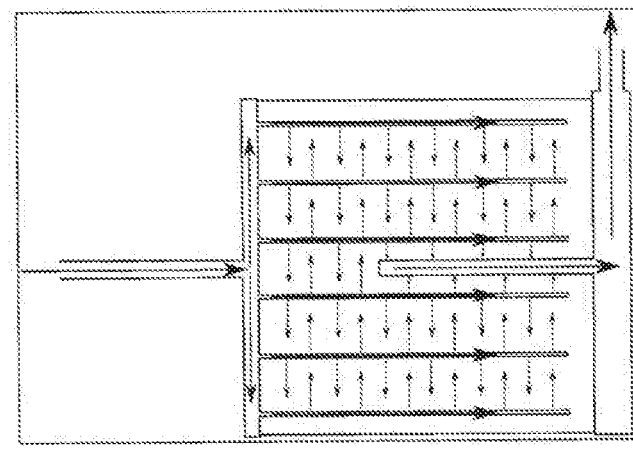
FIG. 6A illustrates a velocity field calculated for use in CFD simulations of fluid flowing through a perfusion chamber.
Figure 6B:
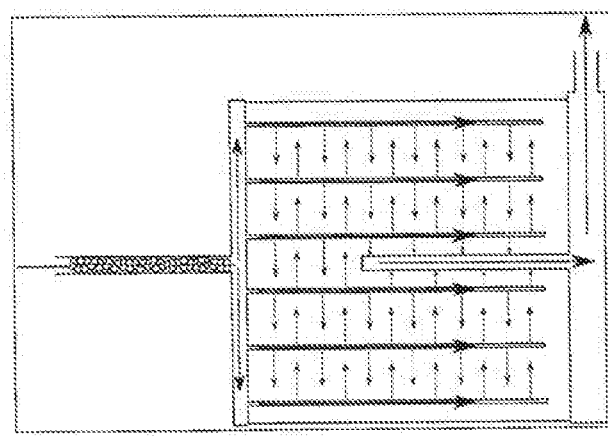
FIGS. 6B-6D show simulated particles representing units of labelled perfusate moving through an perfusion chamber.
Figure 6C:
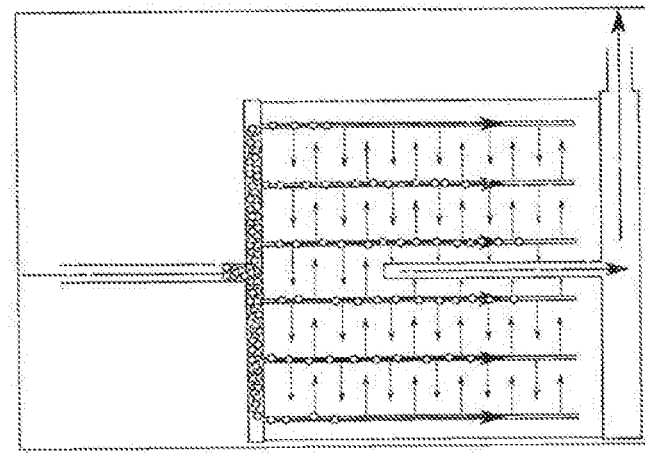
Figure 6D:
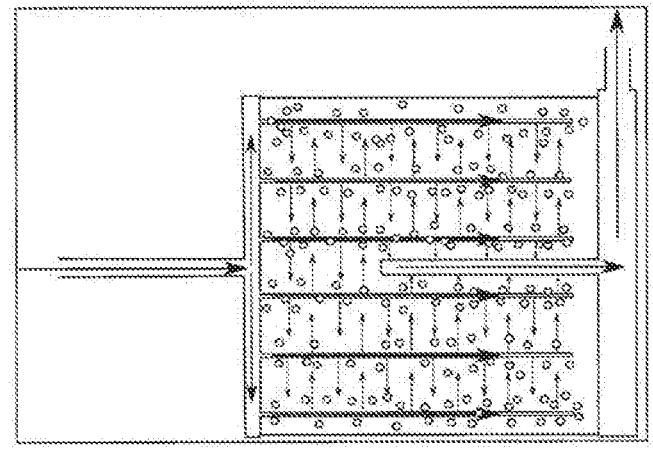

FIG. 6A shows the calculated velocity field (with the magnitude of the velocity of the fluid at each point being represented by the thickness or size of the various arrows) and FIGS. 6B to 6D show the movement of the modelled particles over time as they are subjected to the velocity field and magnetic effects.

The output of the model can then be compared to the desired characteristics, including permeability, of a perfusion chamber given the porosity of the perfusion medium. In general it is useful to define various cost functions which give a quantitative measure of the difference between the model results and desired characteristics of the flow. These cost functions can then be combined to an optimisation function which is minimised. During the minimisation process a minimum value for the cost function is found by varying input parameters and calculating the optimisation function for a number of runs. In a parameter space where the axes represent the different input parameters a function representing the optimisation function at each point can be defined. Gradient descent can be used to find a minimum by following the steepest gradient (greatest change in optimisation function towards a lower value) from each point for which a model is run until such a minimum is reached. Other optimisation methods e.g. such as Runge-Kutta, could be used as well or instead. The above-described techniques for parameter optimisation are well known for different uses, as are methods for avoiding local minima when using such techniques.

For example only, some approximate values for an optimal geometry are provided below:

| Model Parameter | Value |
|---|---|
| Channel length/length of porous material | 0.9 |
| Inflow rate | 400 ml/min |
| Zero-order channel radius | 0.5 mm |
| First-order channel radius | 0 mm |
| Radial channel spacing | 16 mm |
| Circumferential channel spacing | 36 mm |

The calibration test determines whether the scanner is correctly calibrated by comparing the acquired image data to a reference standard. perfusion chamber The calibration procedure is described in more detail below.

Figure 7A:
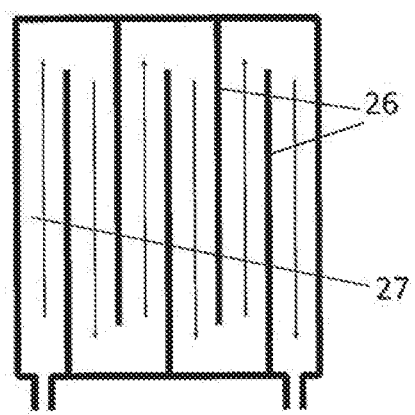
FIG. 7A shows one configuration of a reservoir.
Figure 7B:
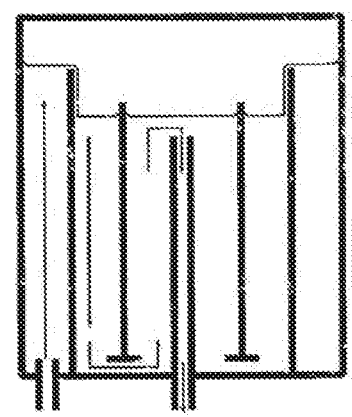
FIG. 7B shows another configuration of a reservoir.

Configurations of a reservoir are shown in FIGS. 7A and 7B. As described briefly above, the perfusate is held within this reservoir for a time after leaving the perfusion chamber and before it is recirculated through the system. The particular structure of the reservoir allows the time between passes of the perfusion chamber to be carefully controlled and allows the perfusate sufficient time to demagnetise before re-entering the labelling chamber. In general, the reservoir provides a winding or tortuous path for the fluid. The length of the path provided is proportional to the time taken for the fluid to pass through the reservoir. Preferably, using a flow rate for the perfusate of around 300-500 ml/min in order to replicate the flow of blood within the body, the time spent within the reservoir chamber should be at least 30 seconds to allow the establishment of fully relaxed magnetisation for the perfusate (the labelled bolus of perfusate must have enough time to return to its equilibrium magnetisation before flowing through the perfusion chamber again).

Figure 7C:
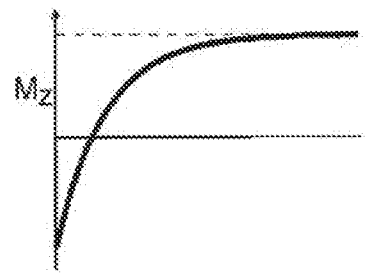
FIG. 7C illustrates the change in magnetisation of the perfusate with time after tagging.

FIG. 7C shows the change in magnetisation of the perfusate with respect to time after tagging. The residence time of the perfusate within the reservoir should preferably be greater than 5 times the longitudinal relaxation time constant T1 to ensure that no residual tag from previous ASL measurements made on the phantom exists when the perfusate exits the reservoir. With this in mind, the size of the reservoir should also be kept to a minimum in order to reduce weight and cost. Some possible configurations of the reservoir are described below. The retention time should preferably be as short as possible while still allowing the perfusate sufficient time to relax.

A simple embodiment is shown in FIG. 7A. Here the fluid simply flows back and forth within the chamber, directed by a number of solid walls 26. In embodiments, a second set of walls, orientated substantially perpendicular to the first set can be located within the reservoir to divide the structure into a number of "streams" through which the water can flow. This may help to prevent sideways flow of fluid within the reservoir which, although it can help with mixing the fluid, will reduce control of the flow time of fluid through the reservoir. The inlet tube can be split into a number of inlets running to each of the different streams. Perfusate then flows from the inlets through the reservoir within its particular stream towards the outlet. In the embodiment shown in 7A the outlet is located at the opposite side of the reservoir to the inlet and also extends from the base of the reservoir (although it can equally extend from the top as can the inlet pipe).

The reservoir may be cylindrical in shape, so that the section of the fluid path 27 immediately following the inlet extends from the outer, tubular, wall of the reservoir to an inner tube placed inside the outer. The reservoir can thus be formed of a number of rings or tubes of acrylic (or of any material that is light enough to transport and waterproof) getting progressively smaller and placed inside one another. The outlet tube may extend from the centre of the cylinder at the base of the reservoir.

An embodiment is shown in FIG. 7B similar to the reservoir described above wherein the tubes forming the walls of the fluid pathways are also shorter towards the middle of the chamber. Because of this, wherever the direction of the fluid flow changes from an upward direction to a downward direction towards the base of the reservoir, the fluid flows over the top of one of the walls and down into the next section of the pathway. The reservoir need not be cylindrical and can be any other shape, such and square or rectangular, within which a series of walls can be placed so as to provide a tortuous path for the perfusate. The number of rings and hence the width of the path provided for the fluid should be chosen to optimise the length of the path taken by the fluid to hold the fluid within the reservoir for the requisite amount of time whilst minimising the weight and size of the reservoir. In theory, a simple tank without a tortuous path can be used as the reservoir; however this is much less effective because the minimum distance that the fluid may have to travel is only equal to the shortest path from the outlet to the inlet. The actual distance travelled by the fluid through the reservoir will also be much more difficult to control. Control of variables is particularly important in systems such as this which are intended for use in a medical setting for calibration purposes. The size of the reservoir must be sufficient to hold enough water to allow a residence time of at least 5 times the longitudinal relaxation time. As an example, if distilled water is used at a flow rate of 400 ml/s then the reservoir will need be capable of containing around 200 ml of water at one time assuming that all fluid follows the tortuous path provided. In reality, due to possible turbulence and other effects as well as the volume taken up by the structures within the reservoir, the volume may need to be larger (and the required volume will change depending on flow rate and the type of perfusate used).

The pump mechanism is shown in-situ in FIG. 1, and as described above the pump itself may share a shielded enclosure with a UV chamber, cooling block, flow-meter and a controller/driver board. Preferably the enclosure is formed of a shielding metal such as aluminium or copper which can effectively shield the elements within from the strong electromagnetic fields in the MRI scanner bore. Any appropriate shielding metal could be used. The pump can be located within the bore of the chamber and thus must be able to withstand the harsh environment within the bore while the scanner is in use. This is achieved using a piezoelectric pump (such as those available from Nitto Kohki Europe Ltd), the shielded enclosure and the particular configuration of the electronics used with the pump.

The application of a voltage to the piezoelectric elements within the pump results in movement of the elements, which in turn move a diaphragm that which pushes fluid through and out of the pump at the desired flow rate. The voltage applied can be adapted, through use of the flow meter and microcontroller, to maintain the flow rate provided by the pump at the desired level. It is possible to adjust the desired flow rate through the phantom for different uses, but in general a flow rate of between 350 and 450 ml/min (and preferably around 400 ml/min) should be used in order to replicate the flow of blood within the body of a subject. However, it will be appreciated that higher or lower flow rates could be used.

For use in calibrating scanners for brain imaging, the perfusion rate within the imaging volume itself should be around 20-80 ml/min/100 g to allow for lower (white matter) and upper (grey matter) perfusion measured within the human brain. Velocity of perfusate within the labelling region should be around 25-30 cm/s, which is similar to the mean blood velocity for an adult cardiac cycle. More than one of any of the components related to the pump system (elements within the shielded enclosure, the amplifier and the power module) can be used. In particular, the use of two or more piezoelectric diaphragm pumps may be desirable.

A microcontroller on the controller/driver board receives input from the flow-meter and adjusts the voltage to the pump in dependence on this input to maintain a desired flow rate. The microcontroller can run firmware with a PID algorithm in order to minimise the "error" or the difference between the flow rate indicated by the flow-meter and the desired flow rate by adjusting the voltage input to the pump. Such algorithms are conventional and will be known to the skilled person.

The cooling block can simply comprise a chamber within the pump enclosure through which the perfusion fluid or some of the perfusion fluid is diverted in order to cool the various electrical components used to support the pump (in particular the power amplifier). Clearly the chamber itself will need to be well sealed so that water cannot reach the electronics. The small increase in temperature of the perfusion fluid will be insignificant and should not affect the capabilities of the system as a whole; however it is possible to include a separate cooling system which houses different fluid that is either static or pumped through a cooling block that is not connected by fluid channels to the main system. Alternatively, any known method for cooling electronics which is suitable for use within an MRI bore can be used.

Figure 8:
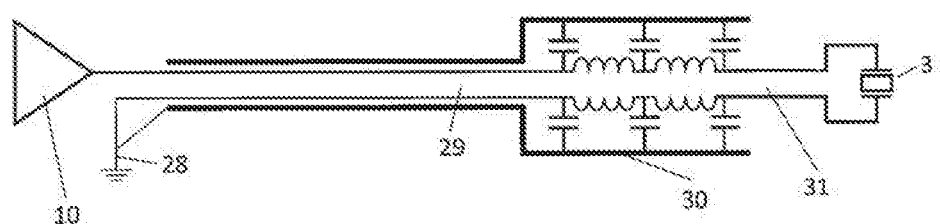
FIG. 8 shows a part of the pump mechanism.

The pump itself is shown in FIG. 8 and can comprise the piezoelectric pump element itself 3 along with a pump power amplifier 10, a ground cable 28 for the power amplifier, a shielded two-core cable 29, a shielded pi filter 30 and an unshielded two-core cable 31 to the pump. This particular configuration of components allows a pump to be used within the MRI bore without the strong electro-magnetic fields interfering with the action of the pump. The pi filter comprises a series of capacitors and inductors connected as shown in the figure. The capacitor and inductor values are carefully chosen so that at the frequency of operation of the MRI scanner (which will typically be around 128 MHz for a 3 T scanner) the impedance of the inductors is high, while the for the capacitors it is very low (as an example, these values may be around 3500-4000 nH and 450-500 pF respectively). This will effectively block the flow of RF currents to the piezoelectric pump and the power amplifier and will instead shunt them to the cable shield and then the ground.

The piezoelectric pump requires bipolar driving voltages which can be provided using a bipolar power supply. The DC-DC converters generally used to generate these voltages, however, contain ferrite which makes them unsuitable for use in the bore of an MRI scanner because of the strong magnetic fields. In order to provide a suitable driving voltage in an MRI compatible pump a single supply driving circuit which can provide +/−150V DC and which does not include ferrite components can be used as a voltage supply to the pump. This may not, however, provide functionality matching that of a pump supplied using a bipolar circuit. As an alternative, one or more of a linear bridge amplifier, a charge pump, an air core inductor based boost converter or a piezoelectric transformer can included in the pump circuitry in order to improve the performance of the single supply driving circuit. A linear bridge amplifier consists of two linear amplifiers, each driving different sides of a load. The input waveforms of the two amplifiers are anti-phase to each other, allowing the bridge amplifier to provide double the voltage swing of the supply rails, and also provide positive and negative voltages across the load. This provides the advantage that only a +150V rail is required.

Alternatively, a separate power supply module can be located outside of the scanner to supply voltage to the pump. The power supply module can comprise one or more batteries (a 11.1V 3S lithium polymer battery is a suitable choice) and one or more high power DC-DC converters which can produce the required +/−150V to drive the pump. The power supply can also soft-switch power to the DC-DC converters. Protection and monitoring circuitry can be included which ensure that magnetic fields near to the scanner do not affect the pump's functionality and that when this functionality is reduced or affected by the proximity of the scanner the power module can be moved. A multi core, shielded cable may connect the power module to the pump and including a cable trap can help to reduce interference from the strong electromagnetic fields while the pump is in use. A cable trap may, for example, be located on the shielded cable near to the pump module end (10-50 cm from the end of the cable). Shielded connectors (such as Lemo connectors) should preferably also be used on the cable.

Figure 9:
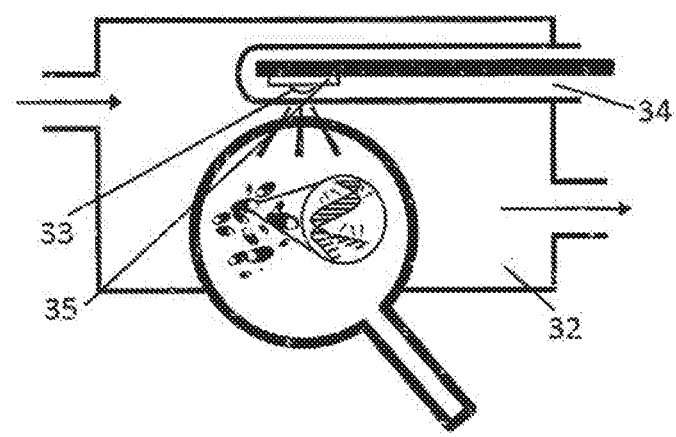
FIG. 9 shows the UV chamber.

FIG. 9 shows the UV chamber in more detail. The design is fairly simple and comprises a chamber 32 through which the perfusate flows (generally located with the pump electronics inside a shielded enclosure). The chamber will preferably be formed of acrylic to allow for easy manufacture and can be shaped in any way (although a tubular enclosure may provide less turbulence. The chamber may be located within the shielded enclosure housing the pump electronics and may be the same as that used to provide the cooling block or may be separate, although locating the UV chamber with the pump electronics will provide a more efficient layout. The chamber can include an air space to allow any gases trapped within the perfusate to escape. In this way the UV chamber can act both as a germicide to kill the bacteria and as a bubble trap.

A UV-C LED 33 producing radiation (which may be fairly low power) is located within a waterproof enclosure 34 extending into the chamber. The wavelength produced should have a wavelength of around 250-300 nm, or any wavelength of radiation effective at destroying bacterial DNA. At least a part of the waterproof enclosure should be substantially transparent to radiation at the wavelength produced by the LED and may be formed of quartz glass. Another material may be used that is at least partially transparent to UV (and in particular UVC), however quartz glass is particularly transparent to UVC and thus is a particularly good choice here. The LED can be mounted on a printed circuit board 35 which, as well as providing mechanical support, can contain a constant current regulator (a 20 mA constant current regulator would be suitable) to provide the correct current to the LED. As the perfusate flows through the chamber it is irradiated with UV-C radiation which acts as a germicide by destroying nucleic acids within the DNA of life-forms within the perfusate. Algae and bacteria build-up within the phantom is thus prevented. The battery supplying the pump can be used to run the UV-C LED or a separate power supply can be provided. A mercury bulb could be used as a germicide in a similar configuration to that described above, however mercury bulbs require high voltages, are fragile and would likely not be suitable for use within an MRI scanner because of the susceptibility of their filaments to vibrations caused by the scanner in use which would tend to degrade the life of the bulb.

Although similar systems have been used to reduce algae build-up in swimming pools and the like, such a system has never before been used in the field of medical imaging and in particular within a phantom to keep perfusate clean and reduce the need for biocidal additives. This may be the first time that the problem of bacterial build-up within a phantom has been considered because phantoms for extensive distribution and long term use for calibration purposes have not yet been developed.

The physical phantom, combined with the flow modelling procedure described above, can be used to provide a homogenised calibration system for MRI scanners in a clinical environment, such as in hospitals. It is conceivable that the system could also be used to calibrate scanners for other applications. Once simulated images of the optimised phantom have been produced, these can represent a "ground truth" and can provide a standard. Images taken of the same phantom (or a phantom that is substantially identical) with different MRI machines can be compared to this standard. A failed calibration test can indicate that a particular MRI machine is not suitable for use in quantitative medical imaging.

In one example, in the event of a failed calibration test a machine is adjusted to bring the images into agreement. In this way, images taken with the calibrated MRI scanners of real subjects can be used to determine quantitative values for properties such as volume rate of flow of blood in different parts of the brain for the first time in a medical setting.

In order to provide a calibration system that is properly standardised, an online service using a reference data or a reference standard traceable to international standards can be provided. This service can be cloud-based, allowing hospitals and clinics or imaging centres to upload data taken of the same phantom with the MRI machines for which they wish to obtain certification. This data can then be processed centrally, as described in more detail below, and an indication provided to the user as to whether or how their machine might need adjusting.

Figure 10:
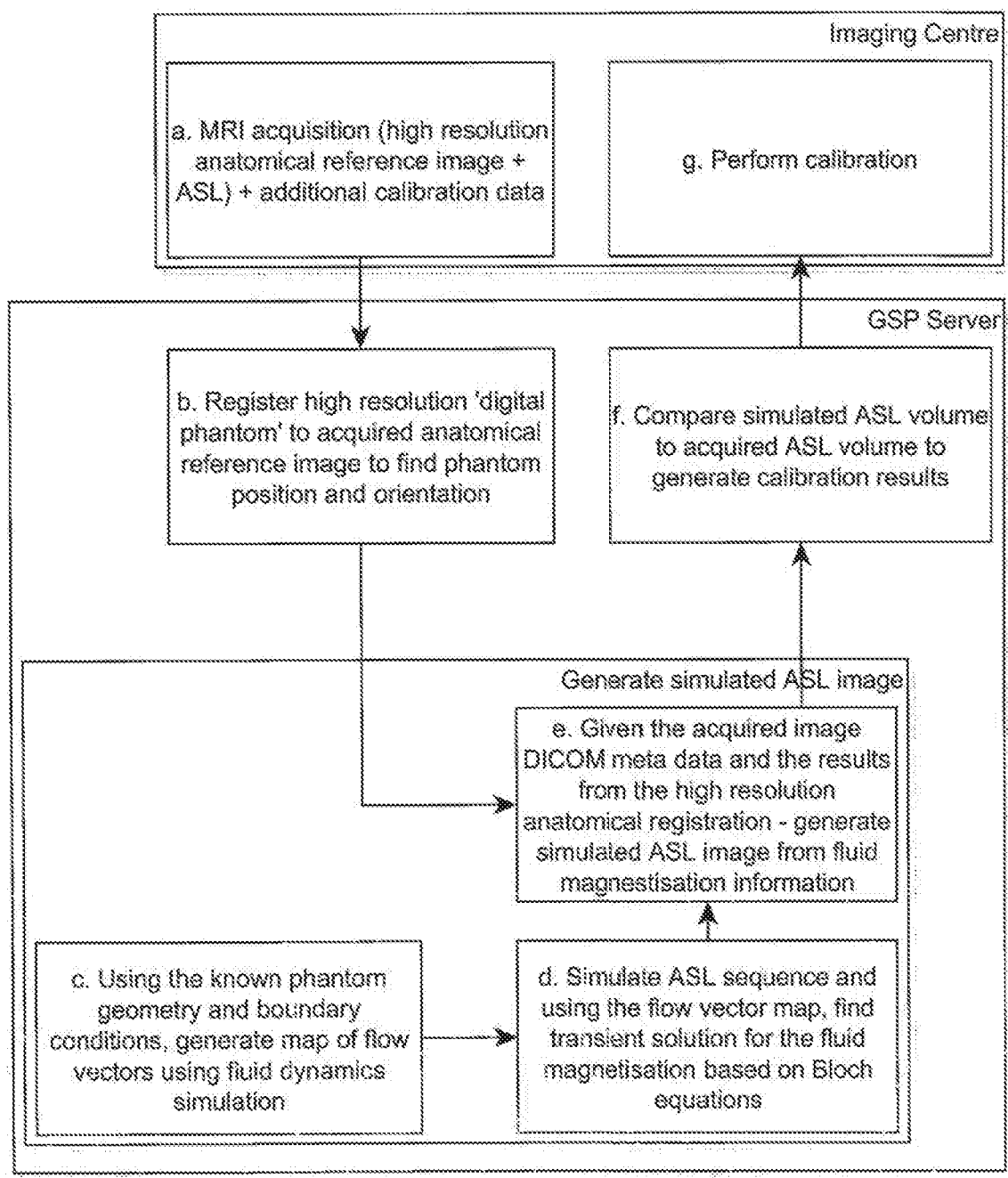
FIG. 10 illustrates a cloud-based calibration procedure.

FIG. 10 shows an example of a calibration method using this type of system. Users can be provided with a web-based interface to facilitate the upload of data and possibly to provide a checklist of steps to be followed in obtaining images, uploading data, which can be in DICOM (Digital Imaging and Communications in Medicine) format (or any other format), along with associated meta-data and calibrating. Users can be asked to log-in, from a website for example, in order to access the system securely. A high resolution anatomical reference image (or possibly multiple reference images) and one or more ASL images are taken with the MRI scanner which requires calibration. The collected data is uploaded to the server where it is registered and compared with the reference "digital phantom" (or reference image) in order to identify orientation and phantom position. The reference data could be static or dynamically created on-the-fly. A simulated ASL image is created as described above in the section dealing with optimising flow geometry of the phantom. This time, however, the orientation and position of the phantom within the MRI scanner in the uploaded image is used to ensure that the simulated image is directly comparable with the real data. Differences in hardware and the specific ASL pulse sequence used by each imaging centre can also be taken into account if necessary by replicating certain conditions when producing the simulated image.

Once the simulated image has been produced this can be compared (still on the server) with the real image in order to automatically generate calibration results. These will indicate whether the scanner in the imaging centre is suitable for providing quantitative ASL information or whether an adjustment might be required. The calibration results are displayed on the web-based interface, are sent to the imaging centre or can be downloaded from the server by a member of staff at the imaging centre. The calibration results may also provide advice as to how to adjust the scanner in the event that calibration is not complete. The advice may be based on information derived from the comparison between the real and simulated images. If necessary, this process can be repeated a number of times. Upload from the scanner can be carried out automatically for scanners connected to the server. Automatic uploads from the scanner may require installation of additional hardware or software on a local network.

The models used to represent the ground truth can be updated and improved as part of the routine maintenance of a centralised repository. Such a system is easily scalable and any improvements will be immediately implemented at all participating locations without the need for any action on the part of the end user. In addition to calibration results, images taken of real, e.g. human subjects using the calibrated machines can be uploaded to the central server and analysed to provide useful statistical (and other) information to centres and the machine manufacturers. Data and calibration results can also be analysed and/or reviewed through the system at a later date which may help to identify common problems. The system can be fully automated as a pipeline to which the images taken at the scanner can be input and the calibration results provided as output.

The idea of using a cloud-based system to calibrate scanning devices by comparing uploaded images with computer simulations of a "ground truth" could be applied to applications other than testing for ASL imaging and need not be limited to this use. The same principle could, for example, be suitable for use in designing phantoms and calibrating scanners for quantitative CA-based perfusion, diffusion based imaging (such as diffusion tensor imaging and tractography) or metabolic and physiological imaging (examples being hyperpolarised MRI and glucose-based MRI). For medical use, all devices are required to meet ISO standards and the calibration engine would need to be designed with these in mind in order to ensure that calibrated scanners are fit for use.

ISO 17025 in particular applies to testing and calibration laboratories. These laboratories must be accredited under this standard in order to be deemed competent to provide their services. This is particularly important in a medical environment where standards are, and must be, adhered to strictly. ISO 17025 includes technical standards which relate to the reliability of the calibration performed.

In the following section additional detail of a calibration process which can ensure a certain standard is provided. Images taken by the scanner are checked against reference images produced using computer modelling to determine whether they can be verified. If the images are able to be verified, the imaging system is considered to be calibrated to an acceptable level of accuracy. The imaging system may be an MRI machine and the process may be for verifying ASL images as described above, however the description is more general and can apply to other imaging machines and methods.

In order for verification and calibration of an MRI scanner (or other scanning equipment) to be sufficiently accurate to meet the strict standards required, it is necessary to link the reference images produced using ground truth models to images taken of the phantom in a way that allows for valid comparison. The description below relates to a general method for calibrating scanning equipment to a particular standard. The application of this method to MRI images taken of a perfusion phantom and a diffusion phantom are separately described, however the validation method is applicable to other types of phantom and scanning equipment.

The ground truth data set may be produced via CFD simulations as described above in the case of a perfusion phantom, where parameters representing the operating conditions of the phantom (such as the temperature, flow rate or pressure) are used as input for the models. Rather than being fixed to particular values, these can be adjusted to take account of changes by monitoring the operating state of the phantom throughout a scan. This is achieved using various sensors which are coupled to the phantom for measuring and reporting values of physical parameters to be used as input to the computer model such as temperature, pressure, and flow rate of fluid within the phantom.

The same process can be followed for other types of phantom (such as a diffusion phantom) by adapting the modelling conditions and the input values (and the sensors) to the particular situation as required. Once sensor data has been collected, this can be used as input to the computer models which produce simulated images, or reference images, of the phantom. These may represent images that would be produced using ASL or other imaging methods depending on the type of scanner and the type of phantom used.

Other types of imaging equipment can be calibrated using a similar method. For example to reproduce a PET image, the signal expected to be received from the particular contrast agent involved can be reproduced using CFD simulations including particles representing the contrast agent and the phantom imaged using a PET camera which detects photons emitted by radioactive tracers caused to flow through the phantom.

Reference images can also be produced by imaging the phantom under controlled conditions (for example using a scanner that is calibrated and has had all aspects of acquisition and data processing validated). In both cases the ground truth data set should effectively represent the "truth" or the real physical condition of the phantom at any particular time. Images can thus be produced from the ground truth data set which represent what the scanner should show if calibrated and functioning properly at a particular time. These images can then be compared to scans taken at the same time to determine whether adjustments to the scanner might need to be made. In some circumstances, the discrepancy between images may also provide clues as to how the scanner may be malfunctioning and advice can be provided to the user (on a computer screen, for example) as to what type of adjustments should be made.

In order to ensure that the calibration process provides accurate results it is important that the operating state of the phantom at any particular time is known. It is also important that images taken with the scanner are timed to properly correspond to this known set of operating conditions. In order to achieve this, one or more sensing devices (such as the flow meter shown in FIG. 1) may be coupled to the phantom in order to monitor the various physical parameters linked to its operating state. This allows the actual operating state of a phantom to be tracked during image acquisition to ensure that simulations use the correct input values for parameters which are likely to affect the appearance of an image taken using the scanner. The change in temperature of the fluid over time, for example, might be used as an input to the model and this will affect the properties of the flow and thus the appearance of the simulated image. The term "operating state" is used to describe the values of physical parameters within the phantom so that if temperature, pressure, and flow rate are measured, the operating state at a particular time will be represented by the values of these parameters. The operating state may also be described by several values of the temperature, pressure, and flow rate in different parts of the phantom. The operating state may vary over time and this change will be recognised by the sensors and logged.

Some examples of parameters which can be monitored and used to define an operating state are the bulk flow rate of the fluid passing through the phantom, the pressure of the fluid within the phantom, the pH of the fluid within the phantom, the concentration of a dissolved compound (such as glucose, sodium, potassium, or lactate) in solution within the fluid, and the temperature of the fluid within the phantom. These measurements can be taken simultaneously with acquiring an image or images of the phantom using the scanning machine. A scan will generally last between 5 and 30 minutes and, during image acquisition, measurements will be taken at intervals using the sensors in order to monitor and continuously update information regarding the physical operating state of the phantom throughout the scan. The interval between measurements will preferably be short in order to achieve near-continuous monitoring. The preferred sampling rate will depend on the nature of the sensor, however in general measurements from the sensors will preferably be collected and logged at least once every 10 seconds, more preferably at least once every second, and even more preferably at least 10 times per second. Smoothing can be achieved by averaging sensor measurements over a certain time period, for example by calculating a mean value within each block of data representing one second of time.

The above described monitoring of data from the sensors allows a user to ensure at all times during the calibration process that the phantom is operating as expected (which may be within strict limits) and makes it possible to adjust its operating state at any time to ensure that this is the case. In order to comply with ISO standards, for example, the phantom may need to be operating under certain conditions and the use of sensing devices can ensure that this is the case.

A control system may be included to allow measurements taken by the sensors to be used as feedback in order to adapt the operating conditions if they fall outside of an acceptable range. An acceptable range for the flow rate might be within 1% of the desired value. Measurements of the flow rate can be taken substantially continuously, and then logged and/or passed to a controller which determines for each measurement whether or not the relevant value for the flow rate falls within the acceptable range. If it does not, the controller can act to either increase or decrease the amplitude of the drive signal to the pump in order to bring the flow rate back into the desired range. The values above and below which a signal to decrease or increase the flow rate is sent may represent a narrower range than that specified by, for example, ISO standards. This will reduce the chances of the actual value falling out of the specified range at any time during a period of measurement.

The desired flow rate may, alternatively, be fixed to a particular value and the controller adapted to adjust it in order to ensure that it stays at this value (increasing or decreasing the amplitude of the drive signal to the pump depending on whether the flow rate measured is below or above the fixed value). Fixing the desired flow rate to a particular value or range may be effected by way of a user interface which can, in embodiments, be accessed online remote from the scanning machinery.

Although the example of a flow rate measurement is described above, similar adjustments to the operation of the phantom may be made to maintain other parameters at a desired value or within a desired range. Several parameters may be controlled simultaneously. The temperature of the phantom may be increased or decreased responsive to signals from the controller by way of a heating or cooling system. A heating system may use a direct heating element to heat the fluid within the phantom or may heat (or cool) fluid which then circulates through the phantom. Pressure may be controlled by increasing flow resistance within the system, for example by closing a valve.

In order to properly control the temperature of the phantom without the need for any feedback mechanism (or in addition to a feedback mechanism), it may be possible to utilise the properties of one or more phase change materials (PCMs). These materials release or absorb energy when changing phase and maintain a consistent temperature as they do so. This phase change period can last for several hours in some cases (depending on the type of material used) which will generally be longer than the time taken to record a scan in an imaging system such as an MRI scanner. Some materials, such as some organic polymers, change phase from a liquid to a solid at around a typical human body temperature and thus may remain at this very precise temperature for an extended period of time. Once these materials start to solidify they can stay at the same temperature for up to several hours until the phase change process is complete. The phantom can be encased in such a material outside of the scan room and the material brought to its phase change temperature at which point the phantom can be transferred into the scanner. The fluid within the phantom should then remain at a constant temperature throughout the scan. Temperature can also be monitored throughout in order to ensure that this is the case.

Operating data from the phantom (measurements of flow rate, temperature, and/or pressure versus time) can be sent to a central repository and logged. This data store may be online (e.g. in the cloud), or may be located in the vicinity of the scanner, or both. The operating data serves as metadata and is associated with images taken of the phantom with the scanner at the same time. Other metadata such as the serial number of the phantom and data regarding the calibration of sensors can also be included. Calibration of the phantom itself, e.g. the on-board sensors, should be performed regularly (for example every year). Metadata can thus be used to determine whether the calibration has lapsed. If this is the case then measurements taken by the sensors will be disregarded, and the image validation stage failed.

Figure 11:
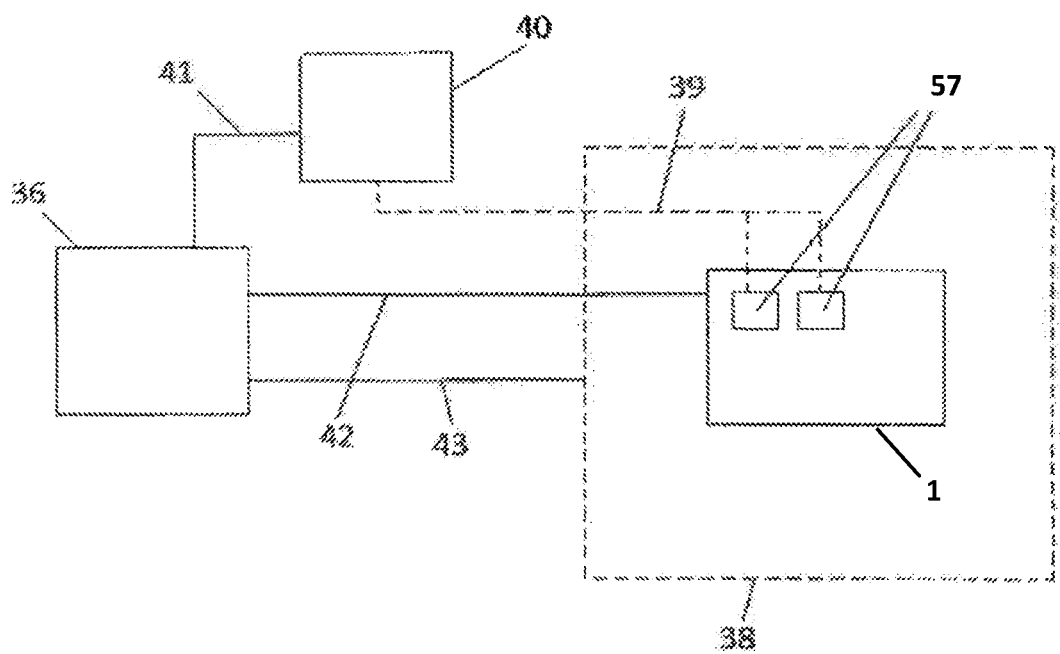
FIG. 11 illustrates a system for image validation.

FIG. 11 shows an example of a system for image validation as it might look during a scan. The system includes a control/logging system 36 which is coupled to sensors 57 and the imaging system 38 being tested. Communications links between the sensor(s) and the control/logging system may be wireless, e.g. may be via Bluetooth® connections 39 to a transceiver box 40 and from there to the control/logging system which may be located outside of the scanning room via another type of connection such as optical fiber 41. This obviates the need for complex wiring within the scanner itself. Bluetooth® connections will also not interfere with the operation of the scanner and likewise the operation of the scanner will not interfere with the transfer of data from the sensor (or sensors) coupled to the phantom to the transceiver box. Of course, data can be passed directly from the sensors to the control/logging system via Bluetooth® if the two are close enough together. Whether this is possible will depend on the layout and features of the MM scan room and including appropriately sized waveguides in line of sight between the scanner bore and the control/logging system. Likewise, optical fiber connections can be hooked up to the sensors directly to convey sensor data directly to the control/logging system.

Connection(s) 42 between the control/logging system and the phantom can allow the control/logging system to send information to the phantom in order to cause an adjustment in its operating state. For example, the control/logging system may receive and log sensor data relating to the flow rate of fluid within the phantom and may process this data to determine that the flow rate is below a desired value. In such a case, the control/logging system may communicate with the pump circuitry to increase the amplitude of the drive signal to the pump which will in turn increase the flow rate as described above.

Connections 43 between the control/logging system and the imaging system are also provided. These allow for synchronisation of the control centre and imaging system time clocks. This synchronisation may be achieved by way of a synchronisation signal sent by the scanner to the control/logging system or an internet based time server may be used to provide a reference time source to which both clocks can be synchronised ahead of or throughout the validation process. Alternatively, the control/logging system may query the scanner for its time, and adjust the control/logging system time such that they are synchronised. This could simply involve a button (implemented in hardware or software) which the user can press when scanning commences to initiate the synchronisation. This ensures, as described above, that the sensor data received from the phantom and used to produce the reference images is representative of the actual operating state of the phantom during the scan.

Figure 12:
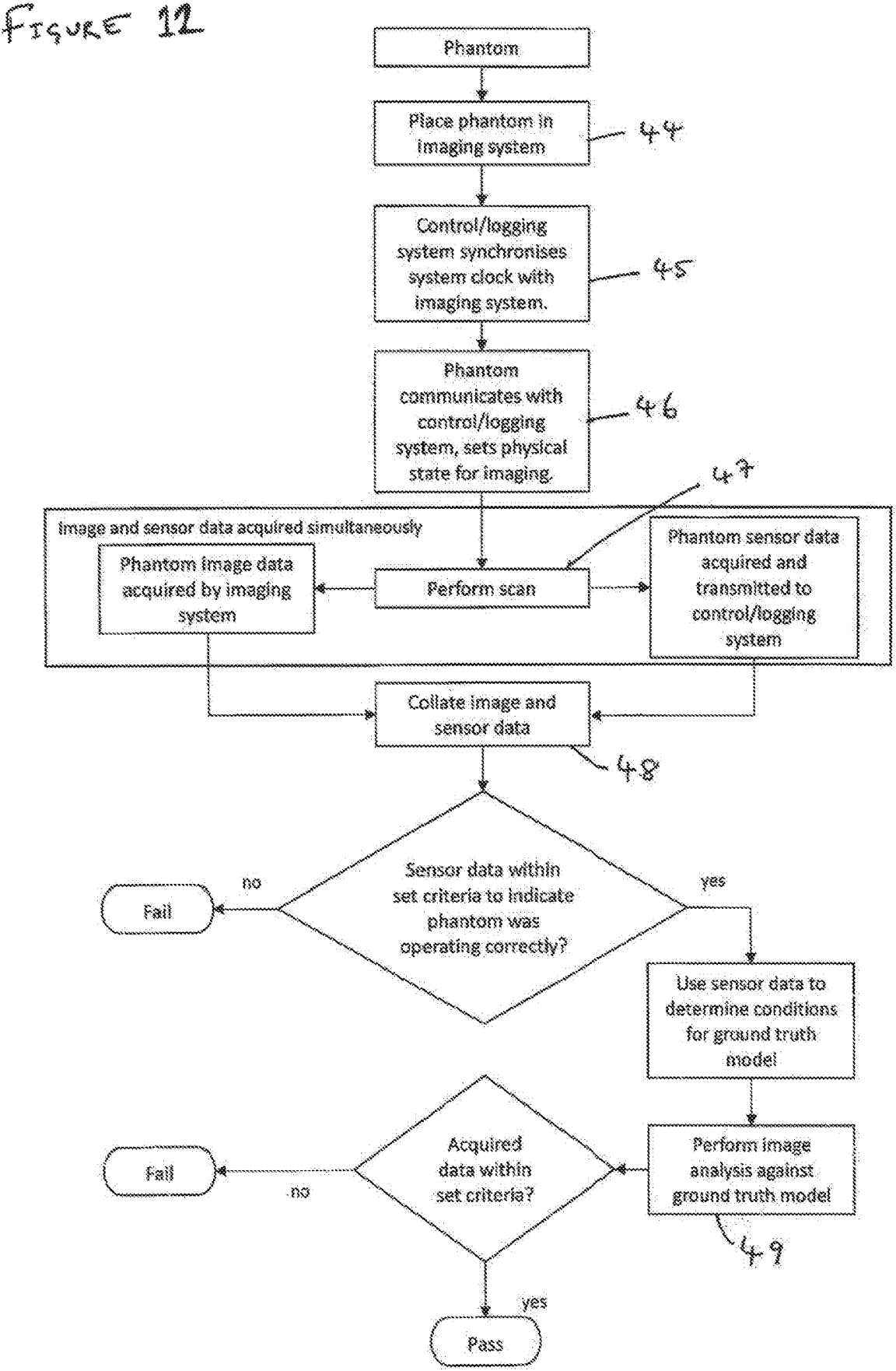
FIG. 12 shows a flowchart of the image validation process.

FIG. 12 provides a flow chart which illustrates the basic method by which image validation can be achieved. The phantom is placed in the imaging system at step 44. The clocks of the imaging system and the control/logging system are synchronised at step 45 before the control/logging system adjusts the operating state of the phantom as to a desired state (or to within a desired range of states) at step 46. Adjusting the operating state of the phantom may involve feedback as described above wherein the sensor data is used to determine whether a particular physical parameter is within a desired range of values and some action taken to increase or decrease the value if it is not. At step 47 the imaging system is used to perform a scan of the phantom. Simultaneously with image acquisition, sensor data is acquired and transmitted to the control/logging system where it is logged and processed. At step 48, the image and sensor data is collated. The sensor data is checked (or may be re-checked if the operating state of the phantom has been controlled during image acquisition already) to ensure that the phantom is operating as it should. The checks may determine whether the phantom was operating within certain required limits necessary to effectively represent a human or animal subject throughout the entire period of the scan. If this is found not to be the case, a fail signal is returned and the image data acquired during the scan is not used to perform a calibration process. At this point the data can be stored or discarded and the phantom checked for technical issues before re-running the scan.

If the phantom has operated as desired throughout the scan, or for at least a specified proportion of the scan time, the measured sensor data can be used to either produce or select a ground truth data set via modelling. The ground truth data set can be used to produce reference images representing the phantom as it should be seen by a scanner that is operating correctly. The appearance of the reference image will depend on the imaging method used.

At step 49 the reference images are compared to the acquired scans to determine whether the two are sufficiently similar. Comparison may be by way of a statistical test such as a t-test to compare data within the regions of interest in the image and ground truth data sets. If the images are not sufficiently similar, then the scanner is not operating correctly and the calibration fails. The scanner must then be checked carefully to determine the cause of the failure. The images and data collected will have been logged and can be used to aid diagnosis of the scanner. The system described above thus ensures that imaging systems that are not operating to a certain standard are not used by medical personnel in situations where they could potentially lead to an incorrect medical diagnosis.

Figure 13:
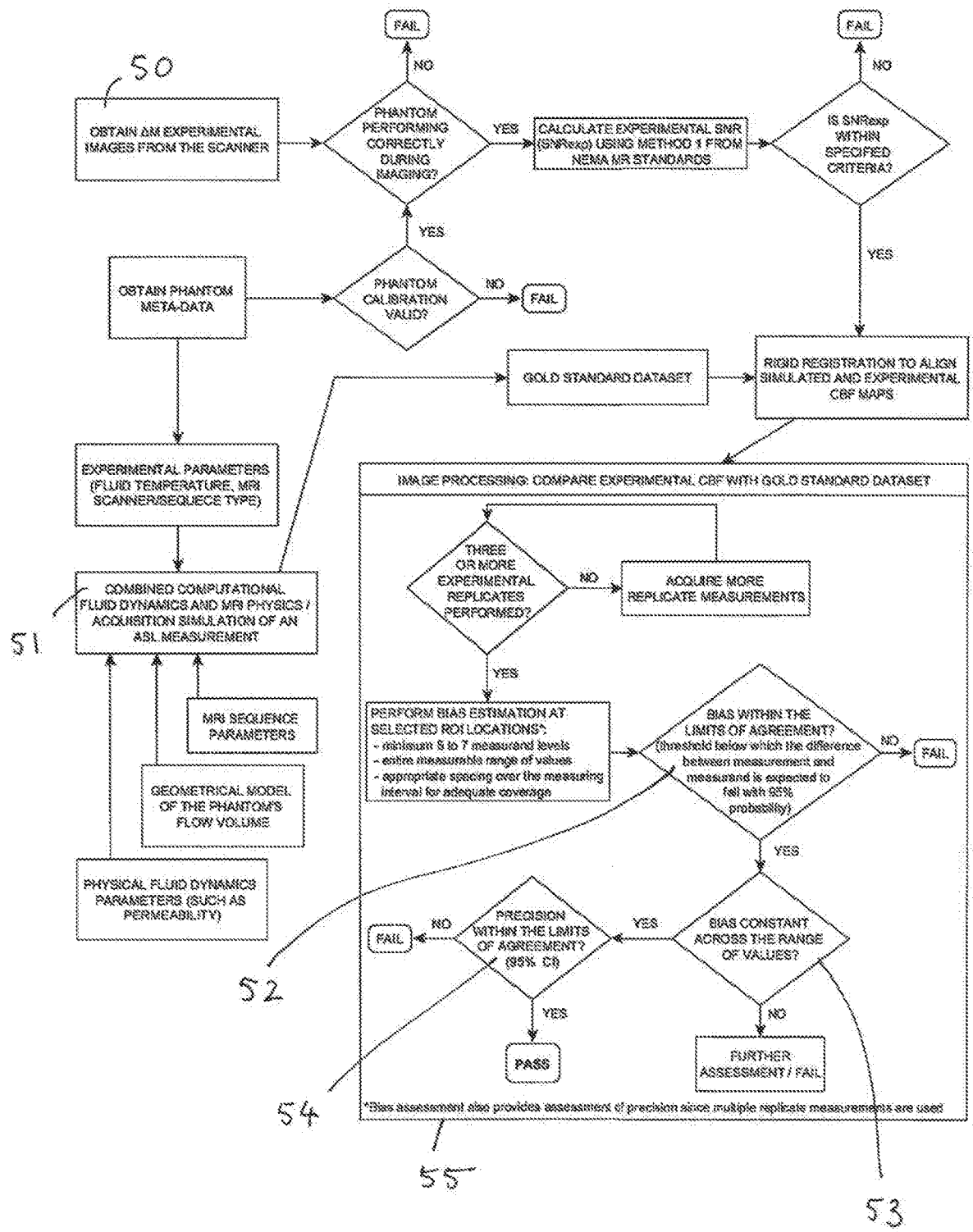
FIG. 13 shows a more detailed flowchart of the image validation process.

FIG. 13 shows a more detailed flow chart of the image validation process, including additional details of the image processing. The flow chart illustrates a case where ASL is used to image a perfusion phantom for calibration of an MRI scanner.

Experimental images are acquired from the scanner at step 50 during which time sensors are used to ensure that the phantom is operating correctly. As described above, this is done by checking whether measured quantities have fallen within a desired range at all times during a scan or for at least a specified proportion of the scan time. The signal to noise ratio in the images may also be checked and the image data rejected if the SNR is not within (or above) a specified range (or value). Metadata is collected and checked to ensure that the phantom calibration is valid. The metadata may include collected sensor data as well as other meta-data related to the phantom such as its serial number. Certain phantoms may be cleared for use with the method so that if the serial number of the phantom shows that it is not an acceptable model or is too old then the validation will fail. The sensor data is used as input for the modelling at step 51 along with MRI sequence parameters, a geometrical model of the phantom's flow volume, and physical fluid dynamics parameters such as permeability of material within the phantom. The output of the model is the ground truth data set used to provide a comparison with the images from the scanner. The reference images produced from the ground truth data set must be properly orientated relative to the scan images in order to provide a valid comparison. This may be achieved using one or more markers on the actual phantom or within the scanning volume of the imaging system which can be recognised in the scanned images method and linked with a known position in the reference image using a rigid or non-rigid registration to align the images.

Box 55 shows some details of the process by which an image taken using the scanner can be compared with a reference image. Several scans can be taken in order to provide a number of comparison images for a more accurate result. Each scan will have its own associated reference images based upon the sensor data collected during each respective scan. In the example shown, at least three replicate images and reference images are produced and compared during the comparison stage. This allows for an assessment of bias (how far away the average of the three values is from the reference value) and of precision (by taking the variance of the three values). More than three replicate scans can be taken which will increase the accuracy of the result but will also increase the time and processing power required. The number of replicates necessary to validate proper calibration of an imaging system to an acceptable standard for use in medical environments may depend on ISO requirements.

Once the image data has been collected and associated reference images produced, bias estimates which indicate the difference between the reference images and the scanned images of the phantom can be calculated for a number of regions of interest within the images. The regions of interest within the images may be predetermined and may correspond to regions where a large variation is expected, for example. At step 52 the bias values are checked to determine whether the measured biases fall within the limits of agreement (in a range within which the bias measurement(s) would be expected to fall with 95% probability if the scanner was correctly calibrated). If this is found to be the case then a pass value is returned and the method moves on to step 53. The bias is checked across the range of values for which measurements have been acquired. In embodiments, the calibration process will result in the equipment failing the calibration if any of the bias measurements fall outside of the limits of agreement. Different percentage values may be used to decide these limits depending on the particular standard of calibration required in each case and on the type of model or instrument used.

The bias values are checked for consistency at step 53. High levels of variation in the bias measurements may indicate unacceptable differences between the reference image and scan data which will cause a fail score to be returned and the images to fail the validation. Variation in bias measurements may also cause the process to move to an additional stage where further assessment is carried out (such as repeating the scanning, modelling, and/or bias determination stages). There may be some leeway in terms of how similar bias results need to be in order for a pass score to be returned. The difference between the highest and lowest values (the range) may be required to be below a predetermined threshold, for example.

If the bias is found to be fairly constant across the range of values tested then the precision is checked at step 54. If the precision (i.e. the uniformity of measurements taken under the same conditions) is within the limits of agreement (to within a 95% confidence interval) then the images are validated and the scanner is deemed to be calibrated to an acceptable level. This may be a level acceptable for use in a medical setting.

The below provides a more specific example of a validation system where the images to be validated are MRI images taken of a perfusion phantom. The phantom may be identical or similar to that described in detail above. Here the bulk flow rate and temperature of the fluid within the phantom are monitored. One or more flow meters are installed in the phantom and may be connected along any of the channels through which fluid passes when the phantom is operating so that fluid passes through the flow meter and flow rate can be recorded. Temperature measurements may be made by way of one or more thermometers extending into the channels through which fluid flows. This way fluid will pass around the thermometer (or around a waterproof container housing the thermometer) giving a more accurate measure of the fluid temperature. Several flow meters and thermometers may be used with the same phantom at different points along the fluid flow path. Measurement data being collected is passed to the data logging system (or control/logging system of FIG. 11). Connection between measurement devices coupled to the phantom and the data logging system may be by way of a Bluetooth® connection between the measurement devices and a transceiver box in the corner of the magnet room as described in general above. Data can then be transferred via fibre optic cable out of the magnet room to the data logging system.

The data logging system is configured to synchronise its system clock to that of the MRI scanner to ensure that the exact conditions in the phantom at the time of each image acquisition is known. It may be that several images are taken with the phantom operating under different conditions (several temperature ranges or flow rate ranges may be tested, for example). This allows the functioning of the MRI scanner to be tested over a range of values for accurate calibration. Once scan images are acquired these can be compared with reference images produced using CFD simulations to ensure that the MRI is producing accurate images. If this is found not to be the case then a fail score is returned by the control/logging system and the MRI scanner can be adjusted and tested again until the simulated images and acquired images match to within an acceptable margin of error. The control/logging system may also control the start time of the scan to ensure that images are taken when the operating state of the phantom is as desired. The start time of the scan can alternatively be manually controlled based on data from the sensors.

A similar method can be used to validate images taken with MRI scanner of a diffusion phantom. These images may be used for quantifying the diffusion of water or other fluids within microstructures in the body (such as white matter tracts). In this case a diffusion phantom is used within which diffusion rates in tissues can be replicated accurately. Diffusion is highly temperature dependant, and as a result it is particularly important in this case for the temperature to be properly monitored and controlled. Non-conductive, MRI compatible thermometers are implanted in the phantom, for example built into the phantom vessel, at one or more locations to measure the temperature of fluid within the phantom. An increase or decrease in the temperature of the phantom within the phantom can be achieved by circulating a heated (or cooled) fluid around the phantom to increase or decrease the temperature to the desired range or value. The data logging works similarly to the logging system described above in the case of a perfusion phantom and again, the data logging system is configured to synchronise its clock to that of the MRI scanner to ensure that the state of the phantom during image acquisition is known.

Embodiments of the present disclosure have been described with particular reference to the examples illustrated. However, it will be appreciated that variations and modifications may be made to the examples described and are within the scope of the present invention as defined by the claims which follow below.

The invention claimed is:

1. An apparatus for validating images, produced by an imaging system, of a phantom, the apparatus comprising:
   one or more sensors for coupling to the phantom, the sensors configured to measure parameters associated with an operating state of the phantom; and
   a control/logging system configured to:
      collect sensor data from the sensors during imaging of the phantom by the imaging system and pass this sensor data as input to a computer model configured to provide a reference image data of the phantom from the sensor data;
      compare image data of the phantom obtained by the imaging system with the reference image data produced using the computer model; and
      return a pass score or a fail score in dependence on the comparison, wherein the phantom is an imaging phantom that replicates conditions within a portion of a living subject imaged by the imaging system and can be utilized to calibrate the or another imaging system.

2. The apparatus of claim 1, wherein the one or more sensors are configured to detect and measure one or more of the temperature of fluid within the phantom, the pressure of fluid within the phantom, and the flow rate of fluid within the phantom.

3. The apparatus of claim 1 further comprising a transceiver box located in the vicinity of the imaging system, wherein sensor data is transferred to the transceiver box via a wireless connection and passed from the transceiver box to the control/logging system using a wired connection.

4. The apparatus of claim 3, wherein the wireless connection is a Bluetooth connection and the wired connection comprises one or more optical fibers.

5. The apparatus of claim 1, wherein the control/logging system further comprises a time clock, and is further configured to synchronise the time clock with a time clock of the imaging system.

6. The apparatus of claim 5, wherein the control/logging system is further configured to synchronise the time clock thereof with the time clock of the imaging system by receiving a synchronisation signal from the imaging system; and/or wherein the control/logging system is further configured to synchronise the time clock thereof with the time clock of the imaging system using an internet based time server to provide a reference time source.

7. The apparatus of claim 1, wherein the imaging system comprises an MRI imaging system, wherein the phantom comprises an MRI imaging phantom, and wherein the MM imaging phantom comprises a closed system through which perfusate can flow, the closed system comprising a pump mechanism for moving perfusate through the closed system, a perfusion chamber, and a reservoir.

\* \* \* \* \*